US009850502B2

(12) United States Patent
Thevelein et al.

(10) Patent No.: US 9,850,502 B2
(45) Date of Patent: Dec. 26, 2017

(54) MUTANT YEAST STRAIN WITH DECREASED GLYCEROL PRODUCTION

(71) Applicants: VIB VZW, Ghent (BE); Katholieke Universiteit Leuven, K.U.Leuven R&D, Leuven (BE)

(72) Inventors: Johan Thevelein, Blanden (BE); Maria Remedios Foulquie-Moreno, Brussels (BE); Georg Hubmann, Groningen (NL)

(73) Assignees: VIB vzw, Ghent (BE); Katholieke Universiteit Leuven, K. U. Leuven R&D, Leuven (BE)

( * ) Notice: Subject to any disclaimer, the term of this patent is extended or adjusted under 35 U.S.C. 154(b) by 11 days.

(21) Appl. No.: 14/431,225

(22) PCT Filed: Sep. 23, 2013

(86) PCT No.: PCT/EP2013/069660
§ 371 (c)(1),
(2) Date: Mar. 25, 2015

(87) PCT Pub. No.: WO2014/048863
PCT Pub. Date: Apr. 3, 2014

(65) Prior Publication Data

US 2015/0225747 A1 Aug. 13, 2015

(30) Foreign Application Priority Data

Sep. 25, 2012 (GB) .................................. 1217028.8
Jun. 6, 2013 (EP) .................................... 13170902

(51) Int. Cl.
*C12P 7/06* (2006.01)
*C07K 14/39* (2006.01)
*C12Q 1/68* (2006.01)
*C07K 14/395* (2006.01)

(52) U.S. Cl.
CPC ................ *C12P 7/06* (2013.01); *C07K 14/39* (2013.01); *C07K 14/395* (2013.01); *C12Q 1/6895* (2013.01); *C12Q 2600/158* (2013.01); *C12Q 2600/16* (2013.01); *Y02E 50/17* (2013.01)

(58) Field of Classification Search
CPC ........................................................ C12P 7/06
See application file for complete search history.

(56) References Cited

U.S. PATENT DOCUMENTS

| | | | |
|---|---|---|---|
| 8,357,835 | B2 | 1/2013 | Leyman et al. |
| 2011/0177570 | A1 | 7/2011 | Baart et al. |
| 2014/0228224 | A1 | 8/2014 | Thevelein et al. |
| 2015/0225747 | A1 | 8/2015 | Thevelein et al. |
| 2015/0307833 | A1 | 10/2015 | Thevelein et al. |
| 2016/0068848 | A1 | 3/2016 | Thevelein et al. |
| 2016/0304888 | A1 | 10/2016 | Thevelein et al. |

FOREIGN PATENT DOCUMENTS

WO 2014048863 A1 3/2014

OTHER PUBLICATIONS

Posas et al., Activation of the yeast SSK2 MAP kinase kinase kinase by the SSK1 two-component response regulator, The EMBO Journal, Mar. 2, 1998, pp. 1385-1394, vol. 17, No. 5.

Horie et al., Phosphorylated Ssk1 Prevents Unphosphorylated Ssk1 from Activating the Ssk2 Mitogen-Activated Protein Kinase Kinase Kinase in the Yeast High-Osmolarity Glycerol Osmoregulatory Pathway, Molecular and Cellular Biology, Sep. 1, 2008, pp. 5172-5183, vol. 28, No. 17.

Nissen et al., Anaerobic and Aerobic Batch Cultivation of *Saccharomyces cerevisiae* Mutants Impaired in Glycerol Synthesis, Yeast, Mar. 30, 2000, pp. 463-74, vol. 16, No. 5, John Wiley & Sons ltd, GB.

Bro et al., In silico aided metabolic engineering of *Saccharomyces cerevisiae* for improved bioethanol production, Metabolic Engineering, Mar. 1, 2006, pp. 102-111, vol. 8 No. 2.

Duitama et al., Towards accurate detection and genotyping of expressed variants from whole transcriptome sequencing data, BMC Genomics, Apr. 12, 2012, p. S6, vol. 13, No. Suppl 2., 10 pages, Biomed Central Ltd, London, UK.

PCT International Search Report, PCT/EP2013/069660, dated Nov. 22, 2013.

PCT International Preliminary Report on Patentability, PCT/EP2013/069660, Date of Issuance Mar. 31, 2015.

PCT Written Opinion of the International Searching Authority, PCT/EP2013/069660, Date of Mailing Nov. 22, 2013.

*Primary Examiner* — Suzanne M Noakes
(74) *Attorney, Agent, or Firm* — TraskBritt, P.C.

(57) ABSTRACT

The disclosure relates to the use of a mutant SSK1 gene encoding a truncated ssk1 protein for the construction of a mutant yeast strain with decreased glycerol production, when compared to the wild-type strain. It relates further to the use of such strains for high-yield bioethanol production, especially in high osmotic media, or on cellulosic hydrolysates, where normal yeast strains do produce a significant amount of glycerol.

10 Claims, 13 Drawing Sheets
(1 of 13 Drawing Sheet(s) Filed in Color)

SEQUENCE LISTING

<160> NUMBER OF SEQ ID NOS: 7

<210> SEQ ID NO 1
<211> LENGTH: 2136
<212> TYPE: DNA
<213> ORGANISM: Saccharomyces cerevisiae
<220> FEATURE:
<221> NAME/KEY: misc_feature
<222> LOCATION: (319)..(321)
<223> OTHER INFORMATION: n is a, c, g, or t
<220> FEATURE:
<221> NAME/KEY: misc_feature
<222> LOCATION: (403)..(405)
<223> OTHER INFORMATION: n is a, c, g, or t
<220> FEATURE:
<221> NAME/KEY: misc_feature
<222> LOCATION: (442)..(444)
<223> OTHER INFORMATION: n is a, c, g, or t
<220> FEATURE:
<221> NAME/KEY: misc_feature
<222> LOCATION: (505)..(507)
<223> OTHER INFORMATION: n is a, c, g, or t
<220> FEATURE:
<221> NAME/KEY: misc_feature
<222> LOCATION: (541)..(543)
<223> OTHER INFORMATION: n is a, c, g, or t
<220> FEATURE:
<221> NAME/KEY: misc_feature
<222> LOCATION: (604)..(606)
<223> OTHER INFORMATION: n is a, c, g, or t

<400> SEQUENCE: 1

```
atgctgaaca gcgcgctgct gtggaaagtg tggctgcgca ttgataacag caccgatgaa     60

gtgaaccagc cgattgcggt gcagtttgat gaaattgata ccgtggatga tctgaaaagc    120

cgctttttc agaaactgag cagcacccgc tggcgcgaaa ttaacgataa cgcgagcatt    180

gcgattggcc tgtatgcgcc gaaatttgat aaccaggcgg ataacaccag cagcaacaac    240

accaacgata acagctgccg cagcaaaagc aacggcgcgg gcagcggcgc gaacctgagc    300

gtgaacagca acaccaaann nagcgtgagc ccgaccgcgg gcagctttgg cctgagcaaa    360

gatctggcga aagatcgcaa cgtgctgcag catccgaaac cgnnncagaa acgcggcgcg    420

ctgtatgatg cgtttgcggc gnnnccgacc gtggcggcga ccaccaacgt ggattttccg    480

ccgaacgaag cgccgatgct gagcnnncag cgcccgtata gcaccagccc gaaacagttt    540

nnngcgacca ccaaaagccc gctgctgcgc tttgcgagcg tgagcccgta tccgaaattt    600

catnnngata accagattat ggcgagcgcg ggcctgacct atgtgagccc gcataacaaa    660

aacaaatata cccgcccgct gattcgcaaa ggcctgaact ttaccaccga aagcgtgaac    720

gattgcacct ataaaattat ttttgaaccg gatgaactgg cgattaacat ttataaagaa    780

ctgtttggca ccatgggcag ccagccggcg agccagccgc tgctgatttt tagcaacgtg    840

aacctgcgcc aggatgtgcc gccgctggat attctgaacg tggtggatta tgtgccgacc    900

aacgaagaaa ttagccagca gaaaacccag ccgaccgatc atggcgcggt gggcgtgttt    960

catctggatg atcatattag cccgggcgaa cagggcctga aacagaccat tggcgataaa   1020

gcggatctga aaggcaaaga tggcaacagc agcccgcagg aatttaaact gattaccgat   1080

gaagaacagc tgcgccgcgc gagccaggaa ctgaaagatg aagaaaaaga tgcggaaagc   1140

ccgtggcagg cgattctgct gctgccgaaa ggctataaag gcggcgtgga ttttcgcaac   1200

aaaccggtgg cgcataccga tagcagcttt aacaacgaag ataccattac ccatagcgaa   1260

ctggaagtga acaccggcag cccgagccag gaaagcggca gcctgaacga agcgggcatt   1320

ggcattaccc agccgatgag cgaagtgcag cgccgcaaag aagatgtgac cccggcgagc   1380
```

```
ccgattctga ccagcagcca gaccccgcat tatagcaaca gcctgtataa cgcgccgttt   1440

gcggtgagca gcccgccgga tccgctgccg aacctgttta ccaccaccag cgaaaaagtg   1500

tttccgaaaa ttaacgtgct gattgtggaa gataacgtga ttaaccaggc gattctgggc   1560

agctttctgc gcaaacataa aattagctat aaactggcga aaaacggcca ggaagcggtg   1620

aacatttgga aagaaggcgg cctgcatctg atttttatgg atctgcagct gccggtgctg   1680

agcggcattg aagcggcgaa acagattcgc gattttgaaa aacagaacgg cattggcatt   1740

cagaaaagcc tgaacaacag ccatagcaac ctggaaaaag gcaccagcaa acgctttagc   1800

caggcgccgg tgattattgt ggcgctgacc gcgagcaaca gccagatgga taaacgcaaa   1860

gcgctgctga gcggctgcaa cgattatctg accaaaccgg tgaacctgca ttggctgagc   1920

aaaaaaatta ccgaatgggg ctgcatgcag gcgctgattg attttgatag ctggaaacag   1980

ggcgaaagcc gcatgaccga tagcgtgctg gtgaaaagcc cgcagaaacc gattgcgccg   2040

agcaacccgc atagctttaa acaggcgacc agcatgaccc cgacccatag cccggtgcgc   2100

aaaaacagca acctgagccc gacccagatt gaactg                              2136
```

```
<210> SEQ ID NO 2
<211> LENGTH: 712
<212> TYPE: PRT
<213> ORGANISM: Saccharomyces cerevisiae
<220> FEATURE:
<221> NAME/KEY: VARIANT
<222> LOCATION: (107)..(107)
<223> OTHER INFORMATION: Mutation from Ser to Arg
<220> FEATURE:
<221> NAME/KEY: VARIANT
<222> LOCATION: (107)..(107)
<220> FEATURE:
<221> NAME/KEY: VARIANT
<222> LOCATION: (135)..(135)
<223> OTHER INFORMATION: Mutation from Thr to Ala
<220> FEATURE:
<221> NAME/KEY: VARIANT
<222> LOCATION: (148)..(148)
<223> OTHER INFORMATION: Mutation from Val to Ala
<220> FEATURE:
<221> NAME/KEY: VARIANT
<222> LOCATION: (169)..(169)
<223> OTHER INFORMATION: Mutation from Pro to Arg
<220> FEATURE:
<221> NAME/KEY: VARIANT
<222> LOCATION: (181)..(181)
<223> OTHER INFORMATION: Mutation from Pro to Ser
<220> FEATURE:
<221> NAME/KEY: VARIANT
<222> LOCATION: (202)..(202)
<223> OTHER INFORMATION: Mutation from Ser to Pro
<220> FEATURE:
<221> NAME/KEY: MISC_FEATURE
<222> LOCATION: (507)..(636)
<223> OTHER INFORMATION: Response regulator receiver domain

<400> SEQUENCE: 2

Met Leu Asn Ser Ala Leu Leu Trp Lys Val Trp Leu Arg Ile Asp Asn
1               5                   10                  15

Ser Thr Asp Glu Val Asn Gln Pro Ile Ala Val Gln Phe Asp Glu Ile
            20                  25                  30

Asp Thr Val Asp Asp Leu Lys Ser Arg Phe Phe Gln Lys Leu Ser Ser
        35                  40                  45

Thr Arg Trp Arg Glu Ile Asn Asp Asn Ala Ser Ile Ala Ile Gly Leu
    50                  55                  60

Tyr Ala Pro Lys Phe Asp Asn Gln Ala Asp Asn Thr Ser Ser Asn Asn
65                  70                  75                  80
```

-continued

```
Thr Asn Asp Asn Ser Cys Arg Ser Lys Ser Asn Gly Ala Gly Ser Gly
                85                  90                  95

Ala Asn Leu Ser Val Asn Ser Asn Thr Lys Xaa Ser Val Ser Pro Thr
            100                 105                 110

Ala Gly Ser Phe Gly Leu Ser Lys Asp Leu Ala Lys Asp Arg Asn Val
        115                 120                 125

Leu Gln His Pro Lys Pro Xaa Gln Lys Arg Gly Ala Leu Tyr Asp Ala
    130                 135                 140

Phe Ala Ala Xaa Pro Thr Val Ala Ala Thr Thr Asn Val Asp Phe Pro
145                 150                 155                 160

Pro Asn Glu Ala Pro Met Leu Ser Xaa Gln Arg Pro Tyr Ser Thr Ser
                165                 170                 175

Pro Lys Gln Phe Xaa Ala Thr Thr Lys Ser Pro Leu Leu Arg Phe Ala
            180                 185                 190

Ser Val Ser Pro Tyr Pro Lys Phe His Xaa Asp Asn Gln Ile Met Ala
        195                 200                 205

Ser Ala Gly Leu Thr Tyr Val Ser Pro His Asn Lys Asn Lys Tyr Thr
    210                 215                 220

Arg Pro Leu Ile Arg Lys Gly Leu Asn Phe Thr Thr Glu Ser Val Asn
225                 230                 235                 240

Asp Cys Thr Tyr Lys Ile Ile Phe Glu Pro Asp Glu Leu Ala Ile Asn
                245                 250                 255

Ile Tyr Lys Glu Leu Phe Gly Thr Met Gly Ser Gln Pro Ala Ser Gln
            260                 265                 270

Pro Leu Leu Ile Phe Ser Asn Val Asn Leu Arg Gln Asp Val Pro Pro
        275                 280                 285

Leu Asp Ile Leu Asn Val Val Asp Tyr Val Pro Thr Asn Glu Glu Ile
    290                 295                 300

Ser Gln Gln Lys Thr Gln Pro Thr Asp His Gly Ala Val Gly Val Phe
305                 310                 315                 320

His Leu Asp Asp His Ile Ser Pro Gly Glu Gln Gly Leu Lys Gln Thr
                325                 330                 335

Ile Gly Asp Lys Ala Asp Leu Lys Gly Lys Asp Gly Asn Ser Ser Pro
            340                 345                 350

Gln Glu Phe Lys Leu Ile Thr Asp Glu Glu Gln Leu Arg Arg Ala Ser
        355                 360                 365

Gln Glu Leu Lys Asp Glu Glu Lys Asp Ala Glu Ser Pro Trp Gln Ala
    370                 375                 380

Ile Leu Leu Leu Pro Lys Gly Tyr Lys Gly Gly Val Asp Phe Arg Asn
385                 390                 395                 400

Lys Pro Val Ala His Thr Asp Ser Ser Phe Asn Asn Glu Asp Thr Ile
                405                 410                 415

Thr His Ser Glu Leu Glu Val Asn Thr Gly Ser Pro Ser Gln Glu Ser
            420                 425                 430

Gly Ser Leu Asn Glu Ala Gly Ile Gly Ile Thr Gln Pro Met Ser Glu
        435                 440                 445

Val Gln Arg Arg Lys Glu Asp Val Thr Pro Ala Ser Pro Ile Leu Thr
    450                 455                 460

Ser Ser Gln Thr Pro His Tyr Ser Asn Ser Leu Tyr Asn Ala Pro Phe
465                 470                 475                 480

Ala Val Ser Ser Pro Pro Asp Pro Leu Pro Asn Leu Phe Thr Thr Thr
                485                 490                 495
```

```
Ser Glu Lys Val Phe Pro Lys Ile Asn Val Leu Ile Val Glu Asp Asn
            500                 505                 510

Val Ile Asn Gln Ala Ile Leu Gly Ser Phe Leu Arg Lys His Lys Ile
        515                 520                 525

Ser Tyr Lys Leu Ala Lys Asn Gly Gln Glu Ala Val Asn Ile Trp Lys
    530                 535                 540

Glu Gly Gly Leu His Leu Ile Phe Met Asp Leu Gln Leu Pro Val Leu
545                 550                 555                 560

Ser Gly Ile Glu Ala Ala Lys Gln Ile Arg Asp Phe Glu Lys Gln Asn
                565                 570                 575

Gly Ile Gly Ile Gln Lys Ser Leu Asn Asn Ser His Ser Asn Leu Glu
            580                 585                 590

Lys Gly Thr Ser Lys Arg Phe Ser Gln Ala Pro Val Ile Ile Val Ala
        595                 600                 605

Leu Thr Ala Ser Asn Ser Gln Met Asp Lys Arg Lys Ala Leu Leu Ser
    610                 615                 620

Gly Cys Asn Asp Tyr Leu Thr Lys Pro Val Asn Leu His Trp Leu Ser
625                 630                 635                 640

Lys Lys Ile Thr Glu Trp Gly Cys Met Gln Ala Leu Ile Asp Phe Asp
                645                 650                 655

Ser Trp Lys Gln Gly Glu Ser Arg Met Thr Asp Ser Val Leu Val Lys
            660                 665                 670

Ser Pro Gln Lys Pro Ile Ala Pro Ser Asn Pro His Ser Phe Lys Gln
        675                 680                 685

Ala Thr Ser Met Thr Pro Thr His Ser Pro Val Arg Lys Asn Ser Asn
    690                 695                 700

Leu Ser Pro Thr Gln Ile Glu Leu
705                 710


<210> SEQ ID NO 3
<211> LENGTH: 1074
<212> TYPE: DNA
<213> ORGANISM: Saccharomyces cerevisiae
<220> FEATURE:
<221> NAME/KEY: CDS
<222> LOCATION: (1)..(1074)

<400> SEQUENCE: 3

atg ctc aat tct gcg tta ctg tgg aag gtt tgg cta cga ata gac aac      48
Met Leu Asn Ser Ala Leu Leu Trp Lys Val Trp Leu Arg Ile Asp Asn
1               5                   10                  15

tcc act gat gaa gta aac caa cca att gct gta cag ttc gat gaa ata      96
Ser Thr Asp Glu Val Asn Gln Pro Ile Ala Val Gln Phe Asp Glu Ile
            20                  25                  30

gat act gtt gat gat ttg aag agc agg ttt ttt cag aaa ctg agt tcg     144
Asp Thr Val Asp Asp Leu Lys Ser Arg Phe Phe Gln Lys Leu Ser Ser
        35                  40                  45

act cga tgg cga gaa att aac gat aat gct tcc att gca ata ggc ctc     192
Thr Arg Trp Arg Glu Ile Asn Asp Asn Ala Ser Ile Ala Ile Gly Leu
    50                  55                  60

tac gca cct aaa ttt gac aat caa gcc gac aat acc agt agt aac aac     240
Tyr Ala Pro Lys Phe Asp Asn Gln Ala Asp Asn Thr Ser Ser Asn Asn
65                  70                  75                  80

act aac gat aat agt tgt cga agt aag agt aac ggt gct gga agt ggc     288
Thr Asn Asp Asn Ser Cys Arg Ser Lys Ser Asn Gly Ala Gly Ser Gly
                85                  90                  95
```

-continued

```
gcc aac ctt tcc gtt aat agc aat acc aag agt tca gtg agc ccc aca      336
Ala Asn Leu Ser Val Asn Ser Asn Thr Lys Ser Ser Val Ser Pro Thr
            100                 105                 110

gca gga tca ttt ggt ctt tca aaa gac ctt gca aag gac agg aat gtt      384
Ala Gly Ser Phe Gly Leu Ser Lys Asp Leu Ala Lys Asp Arg Asn Val
        115                 120                 125

ctc cag cat cct aaa cct acg cag aaa aga gga gca tta tac gac gcc      432
Leu Gln His Pro Lys Pro Thr Gln Lys Arg Gly Ala Leu Tyr Asp Ala
    130                 135                 140

ttt gcc gcc gcg ccg aca gtg gcc gcg act acc aat gtg gat ttt cct      480
Phe Ala Ala Ala Pro Thr Val Ala Ala Thr Thr Asn Val Asp Phe Pro
145                 150                 155                 160

ccc aac gag gcg cca atg cta agc ccg caa aga cca tac tct act agt      528
Pro Asn Glu Ala Pro Met Leu Ser Pro Gln Arg Pro Tyr Ser Thr Ser
                165                 170                 175

cct aaa cag ttt cca gca aca act aaa agt ccg tta ctg cga ttt gcc      576
Pro Lys Gln Phe Pro Ala Thr Thr Lys Ser Pro Leu Leu Arg Phe Ala
            180                 185                 190

tca gtc tca ccc tac cct aaa ttt cat cct gat aat caa att atg gca      624
Ser Val Ser Pro Tyr Pro Lys Phe His Pro Asp Asn Gln Ile Met Ala
        195                 200                 205

tca gct ggt ctt aca tac gtc tca ccg cat aat aaa aat aaa tac aca      672
Ser Ala Gly Leu Thr Tyr Val Ser Pro His Asn Lys Asn Lys Tyr Thr
    210                 215                 220

agg ccg ttg att aga aaa ggt tta aat ttt acc aca gaa tca gtt aat      720
Arg Pro Leu Ile Arg Lys Gly Leu Asn Phe Thr Thr Glu Ser Val Asn
225                 230                 235                 240

gat tgc act tat aaa atc atc ttt gaa ccg gat gaa ttg gct att aac      768
Asp Cys Thr Tyr Lys Ile Ile Phe Glu Pro Asp Glu Leu Ala Ile Asn
                245                 250                 255

ata tat aag gaa cta ttc gga acc atg ggt tcc caa cct gca tcg cag      816
Ile Tyr Lys Glu Leu Phe Gly Thr Met Gly Ser Gln Pro Ala Ser Gln
            260                 265                 270

cct ttg ctg ata ttt tcg aat gtt aat tta cgc cag gat gta ccg cct      864
Pro Leu Leu Ile Phe Ser Asn Val Asn Leu Arg Gln Asp Val Pro Pro
        275                 280                 285

tta gat atc tta aat gtt gta gac tat gtt cct acg aat gaa gaa att      912
Leu Asp Ile Leu Asn Val Val Asp Tyr Val Pro Thr Asn Glu Glu Ile
    290                 295                 300

tcg cag cag aaa act caa cca aca gac cat ggg gcc gtt ggt gtt ttt      960
Ser Gln Gln Lys Thr Gln Pro Thr Asp His Gly Ala Val Gly Val Phe
305                 310                 315                 320

cat cta gac gat cat att tct ccg ggg aac aag gtc tta agc aaa caa     1008
His Leu Asp Asp His Ile Ser Pro Gly Asn Lys Val Leu Ser Lys Gln
                325                 330                 335

ttg gtg ata aag cag atc tta aag gta aag atg gca ata gca gcc ctc     1056
Leu Val Ile Lys Gln Ile Leu Lys Val Lys Met Ala Ile Ala Ala Leu
            340                 345                 350

agg aat tta aat taa taa                                             1074
Arg Asn Leu Asn
        355
```

<210> SEQ ID NO 4
<211> LENGTH: 356
<212> TYPE: PRT
<213> ORGANISM: Saccharomyces cerevisiae

<400> SEQUENCE: 4

```
Met Leu Asn Ser Ala Leu Leu Trp Lys Val Trp Leu Arg Ile Asp Asn
1               5                   10                  15

Ser Thr Asp Glu Val Asn Gln Pro Ile Ala Val Gln Phe Asp Glu Ile
            20                  25                  30

Asp Thr Val Asp Asp Leu Lys Ser Arg Phe Phe Gln Lys Leu Ser Ser
        35                  40                  45

Thr Arg Trp Arg Glu Ile Asn Asp Asn Ala Ser Ile Ala Ile Gly Leu
    50                  55                  60

Tyr Ala Pro Lys Phe Asp Asn Gln Ala Asp Asn Thr Ser Ser Asn Asn
65                  70                  75                  80

Thr Asn Asp Asn Ser Cys Arg Ser Lys Ser Asn Gly Ala Gly Ser Gly
                85                  90                  95

Ala Asn Leu Ser Val Asn Ser Asn Thr Lys Ser Ser Val Ser Pro Thr
            100                 105                 110

Ala Gly Ser Phe Gly Leu Ser Lys Asp Leu Ala Lys Asp Arg Asn Val
        115                 120                 125

Leu Gln His Pro Lys Pro Thr Gln Lys Arg Gly Ala Leu Tyr Asp Ala
    130                 135                 140

Phe Ala Ala Ala Pro Thr Val Ala Ala Thr Thr Asn Val Asp Phe Pro
145                 150                 155                 160

Pro Asn Glu Ala Pro Met Leu Ser Pro Gln Arg Pro Tyr Ser Thr Ser
                165                 170                 175

Pro Lys Gln Phe Pro Ala Thr Thr Lys Ser Pro Leu Leu Arg Phe Ala
            180                 185                 190

Ser Val Ser Pro Tyr Pro Lys Phe His Pro Asp Asn Gln Ile Met Ala
        195                 200                 205

Ser Ala Gly Leu Thr Tyr Val Ser Pro His Asn Lys Asn Lys Tyr Thr
    210                 215                 220

Arg Pro Leu Ile Arg Lys Gly Leu Asn Phe Thr Thr Glu Ser Val Asn
225                 230                 235                 240

Asp Cys Thr Tyr Lys Ile Ile Phe Glu Pro Asp Glu Leu Ala Ile Asn
                245                 250                 255

Ile Tyr Lys Glu Leu Phe Gly Thr Met Gly Ser Gln Pro Ala Ser Gln
            260                 265                 270

Pro Leu Leu Ile Phe Ser Asn Val Asn Leu Arg Gln Asp Val Pro Pro
        275                 280                 285

Leu Asp Ile Leu Asn Val Val Asp Tyr Val Pro Thr Asn Glu Glu Ile
    290                 295                 300

Ser Gln Gln Lys Thr Gln Pro Thr Asp His Gly Ala Val Gly Val Phe
305                 310                 315                 320

His Leu Asp Asp His Ile Ser Pro Gly Asn Lys Val Leu Ser Lys Gln
                325                 330                 335

Leu Val Ile Lys Gln Ile Leu Lys Val Lys Met Ala Ile Ala Ala Leu
            340                 345                 350

Arg Asn Leu Asn
        355
```

<210> SEQ ID NO 5
<211> LENGTH: 391
<212> TYPE: PRT
<213> ORGANISM: Saccharomyces cerevisiae

```
<220> FEATURE:
<221> NAME/KEY: VARIANT
<222> LOCATION: (164)..(164)
<223> OTHER INFORMATION: Mutation from Leu to Pro

<400> SEQUENCE: 5

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Pro Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365
```

```
Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 6
<211> LENGTH: 719
<212> TYPE: PRT
<213> ORGANISM: Saccharomyces cerevisiae
<220> FEATURE:
<221> NAME/KEY: VARIANT
<222> LOCATION: (107)..(107)
<223> OTHER INFORMATION: Mutation from PRO to SER
<220> FEATURE:
<221> NAME/KEY: VARIANT
<222> LOCATION: (274)..(274)
<223> OTHER INFORMATION: Mutation from HIS to TYR

<400> SEQUENCE: 6

Met Ser Gly Met Gly Ile Ala Ile Leu Cys Ile Val Arg Thr Lys Ile
1               5                   10                  15

Tyr Arg Ile Thr Ile Ser Phe Asp Tyr Ser Thr Leu Met Ser Pro Phe
            20                  25                  30

Phe Leu Phe Leu Met Met Pro Thr Thr Leu Lys Asp Gly Tyr Arg Met
        35                  40                  45

Asn Ser Gln Val Asn Glu Asp Ala Ile Gly Ile Asn Leu Asp Leu Ser
    50                  55                  60

Leu Pro Thr His Ile Ser Pro Thr Thr Gly Ser Glu Ser Ala Ser Gly
65                  70                  75                  80

Ser Asn Ala Ser Thr Leu Arg Asn Asp Gly Asn Ala Leu Asp Gly Gly
                85                  90                  95

Leu Leu Arg Thr Ser Ala Ala Ile Ser Ala Ser Thr Gly Thr Ser Gln
            100                 105                 110

Pro Thr Glu Thr Ile Gly Glu Lys Leu Ser Asn Glu Glu Arg Val Asn
        115                 120                 125

Ser Asn Val Ser Ala Ser Asn Ser Thr Thr Ala Gly Thr Gly Arg Met
    130                 135                 140

Leu Ser Gln Ser Leu Thr Asn Asp Ser Pro Ser Asn Glu Ile Ser Thr
145                 150                 155                 160

Asp Gln Leu Lys Ile Phe Gln Arg Met Asp Glu Met Ser Ala Arg Met
                165                 170                 175

Ile Glu Met Glu Glu Ser Phe Asn Lys Leu Ser Asn Lys Ile Ala Glu
            180                 185                 190

Gln Asn Thr Met Val Leu Asn Leu Lys Gln Asp Asn Tyr Lys Val Met
        195                 200                 205

Asn Lys Leu Asn Ile Leu Leu Lys Leu Val Ala Gln Pro Ser Ala Arg
    210                 215                 220

Pro Ser Thr Asn Asn Ala Gln Asn Lys Leu Ala Ile Glu Leu Leu Asn
225                 230                 235                 240

Ser Ile Ser Ala Val Ser Ser Ala Tyr Leu Gln Lys Met Gln Asn Asn
                245                 250                 255

Gly Ser Gly Arg Gln His Thr Ala Asp Leu Cys Thr Gly Asp Ser Asn
            260                 265                 270

Thr Tyr Ser Gly Ile Asn Gln His Arg Thr Thr Asn Gly Thr Ile Asp
        275                 280                 285

Val Asn Thr Asn Thr Ala Gln Leu Asn Asn Gln Phe Ser Asn Ala Leu
    290                 295                 300
```

```
Asn Thr Ile Leu Pro Asp Gln Gln His Asn Arg Asn Asn Val Ser Gln
305                 310                 315                 320

Asn Ile Asn Gln Ser Leu Pro Asn Arg Gln Leu Gly Pro Val Ile Asn
                325                 330                 335

Thr Gln Ala Asn Gln Asn Gln Ser Gln Val Leu Ile His Asn Thr Asn
            340                 345                 350

Thr His Gln Gln Val Asn Arg Ser Pro Ile Ser Phe Pro Asn Ala Ser
        355                 360                 365

Thr Asp Lys Pro Phe Lys Leu Asn Pro Asn Gly Ile Lys Arg Arg Arg
    370                 375                 380

Arg Asn Thr Gln Ser Asn Asn Asn Ala Ser Thr Asn Asp His Ala Ser
385                 390                 395                 400

Ala Ala Gln Lys Pro Ile Ser Ala Leu Ser Pro Leu Thr Asn Ser His
                405                 410                 415

Asn Ser Thr Thr Ser Met Asn Tyr Thr Asn Ser Ser Ile His Ser Gly
            420                 425                 430

Val Thr Ser Ala Ser Asn Ser Phe His Asp Leu Asn Ser Leu Asn Asn
        435                 440                 445

Phe Gly Thr Thr Thr Ala Leu Ser Leu Pro Ser Leu Ala Leu Asp Asn
    450                 455                 460

Ala Ser Phe Pro Pro Asn Gln Asn Val Ile Pro Pro Ile Ile Asn Asn
465                 470                 475                 480

Thr Gln Gln Pro Leu Ser Phe Ser Gln Leu Ile Asn Gln Asp Ser Thr
                485                 490                 495

Thr Ser Glu Leu Leu Pro Ser Gly Lys Ser Gly Val Asn Thr Asn Ile
            500                 505                 510

Val Asn Arg Asn Arg Ala Ser Thr Leu Pro Ser Tyr Pro Lys Pro Met
        515                 520                 525

Thr Val Lys Ser Asn Val Asp Asp Asp Gly Tyr Gln Glu Asp Asp Asp
    530                 535                 540

Asp Asp Gly Asp Asp Glu Gly Asp Gly Arg Asp Asn Glu Glu Asp Ser
545                 550                 555                 560

Thr Ala Glu Glu Asp Glu Val Asp Asp Glu Ile Glu Thr Asp Met Lys
                565                 570                 575

Asn Ala Ser Ile Asn Lys Arg Arg Arg Ser Leu His His Lys Lys Ser
            580                 585                 590

Asn Ser Leu Asn Gly Arg Arg Lys Leu His Gly Glu Ser Ala Thr Lys
        595                 600                 605

Pro Asn Ile Asn Ser Asp Leu His Tyr Arg Ile Leu Lys Ala Pro Thr
    610                 615                 620

Asp Val Lys Thr Ile Trp Glu Glu Tyr Asp Thr Gly Ile Arg Gly Lys
625                 630                 635                 640

Pro Ser Ile Lys His Leu Glu Ala Lys Tyr Gly Asn Lys Trp Arg Leu
                645                 650                 655

Asn Lys Asn Lys Lys Thr Phe Ser Arg Arg Lys Arg Leu Tyr Lys Phe
            660                 665                 670

Ile Leu Asn Gly Met Glu Arg Gly Lys Thr Ala Gln Glu Met Ile Glu
        675                 680                 685

Thr Leu Glu Asn Lys Arg Leu Tyr Lys Asp Asp Glu Asp Gly Glu Val
    690                 695                 700

Lys Lys Arg Thr Ile Gly Trp Leu Gln Glu Ser Leu Ala Gly Ile
705                 710                 715
```

```
<210> SEQ ID NO 7
<211> LENGTH: 452
<212> TYPE: PRT
<213> ORGANISM: Saccharomyces cerevisiae
<220> FEATURE:
<221> NAME/KEY: VARIANT
<222> LOCATION: (110)..(110)
<223> OTHER INFORMATION: Mutation from Arg to Gln
<220> FEATURE:
<221> NAME/KEY: VARIANT
<222> LOCATION: (269)..(269)
<223> OTHER INFORMATION: Mutation from Pro to Gln

<400> SEQUENCE: 7

Met Gly Arg Arg Lys Ile Glu Ile Glu Pro Ile Lys Asp Asp Arg Asn
1               5                   10                  15

Arg Thr Val Thr Phe Ile Lys Arg Lys Ala Gly Leu Phe Lys Lys Ala
            20                  25                  30

His Glu Leu Ser Val Leu Cys Gln Val Asp Ile Ala Val Ile Ile Leu
        35                  40                  45

Gly Ser Asn Asn Thr Phe Tyr Glu Tyr Ser Ser Val Asp Met Ser Asn
    50                  55                  60

Leu Leu Asn Val His Gln Asn Asn Thr Asp Leu Pro His Asn Ile Ile
65                  70                  75                  80

Glu Pro Ser Asp Tyr Gly Asp Tyr Val Lys Lys Pro Arg Val Val Leu
                85                  90                  95

Asn Glu Arg Lys Arg Arg Arg Arg Arg Ala Thr Val Leu Gln Pro Ala
            100                 105                 110

Ser His Ser Gly Ser Cys Thr Val Ser Ser Gln Asp Ser Ser Ser Val
        115                 120                 125

Gln Asn Asn Gly Asn Leu Ser Ala Pro Leu Ala Ser Asn Asp Ala Gly
    130                 135                 140

Asn Ala Gly Val Ser Thr Pro Leu Val His Cys His Gly Ala Ile Ser
145                 150                 155                 160

Arg Ser Gly Ser Asn His Ser Asp Cys Ala Arg Asn Ser Ala Asp Tyr
                165                 170                 175

Gln Met Leu Gln Gly Gly Leu Asn Ser Gly Gly Ser Phe His Ala Asn
            180                 185                 190

Asp Tyr Lys Glu Ser Val Asp Gln Gln His Val Ala Asn Glu Ala Ile
        195                 200                 205

His Arg Asn Phe Met Asn Lys Arg Ile Arg Pro Asp Thr His Leu Leu
    210                 215                 220

Leu Ser Glu Ser Asn His Ser Asn Tyr His Asn Phe Tyr Pro Ser Pro
225                 230                 235                 240

Tyr Glu Asn Leu Pro Lys Pro Ser Leu Pro Ala Ser Leu Val Gly Asn
                245                 250                 255

Ile Pro Ser Phe Gln Ser Gln Phe Val Gln Val Ile Gln Ala Asn Ser
            260                 265                 270

Asn Pro Met Gly Lys Gly Phe Asn Gly Thr Gly Asp Ser Glu Ser Phe
        275                 280                 285

Glu Ala Lys Gln Lys Ile His Pro Thr Val Ala Ile Ser Asn Thr Leu
    290                 295                 300

Glu Gly Pro Ala Pro Val Gln Ala Met Val His His Leu His Gln Leu
305                 310                 315                 320

Asn Ser Asn Arg Gly Lys Leu Ser Gly Lys Pro Tyr Leu Lys Leu Asn
                325                 330                 335
```

-continued

```
Ile Pro Lys Ala Thr Asn Asp Ala Cys Gln Arg Ser Pro Ala Met Tyr
            340                 345                 350

Ser Gly Thr Ala Ser Pro Lys Thr Asp Val Gln Ala Thr Pro Asn Gln
        355                 360                 365

Met Leu Ala Ser Asn Met Ser Ser Pro Leu Ser Arg Ser Lys Phe Leu
    370                 375                 380

Gly Phe Lys Asn Asn Asp Met Asp Asp Leu Tyr His Asn Gly Arg Cys
385                 390                 395                 400

Gly Ser Thr Tyr Val Asn Asn Lys Thr Phe Phe Leu Lys Pro Pro Ile
                405                 410                 415

Gly Arg Pro Pro Lys Phe Pro Lys Ser Pro Ser Ser Ser Ile Val Val
            420                 425                 430

Phe Pro Ser Ser Val Ala Ser Ser Thr Leu Lys Ser Thr Ser Ser Thr
        435                 440                 445

Asn Ser Pro Asp
    450
```

MUTANT YEAST STRAIN WITH DECREASED GLYCEROL PRODUCTION

CROSS-REFERENCE TO RELATED APPLICATIONS

This application is a national phase entry under 35 U.S.C. §371 of International Patent Application PCT/EP2013/069660, filed Sep. 23, 2013, designating the United States of America and published in English as International Patent Publication WO 2014/048863 A1 on Apr. 3, 2014, which claims the benefit under Article 8 of the Patent Cooperation Treaty and under 35 U.S.C. §119(e) to Great Britain Patent Application Serial No. 1217028.8, filed Sep. 25, 2012, and European Patent Application Serial No. 13170902.4, filed Jun. 6, 2013.

TECHNICAL FIELD

The application relates to biotechnology and the use of a mutant SSK1 gene encoding a truncated ssk1 protein for the construction of a mutant yeast strain with decreased glycerol production, when compared to the wild-type strain. It relates further to the use of such strains for high-yield bioethanol production, especially in high osmotic media, or on cellulosic hydrolysates, where normal yeast strains do produce a significant amount of glycerol.

BACKGROUND

Up to now, the targeted genetic engineering of microorganisms has concentrated largely on the modification of structural genes encoding enzymes in metabolic pathways. This has been done either by up- or down-regulation of gene expression or by modification of kinetic characteristics, substrate specificity or regulatory properties of the constituent enzymes (Nevoigt, 2008). However, targeted engineering has shown only limited success when it comes to complex traits determined by multiple genes and largely unknown regulatory networks. In fact, evolutionary engineering has often been used as a strategy to address such phenotypes difficult to engineer in a rational way. In addition, attempts have been made to engineer regulatory factors in order to simultaneously and randomly alter the regulation of many genes at a time.

SUMMARY

Transcription factor engineering has been used to improve ethanol tolerance and yield in *Saccharomyces cerevisiae* (Alper et al., 2006). However, the changed genotype phenotype relationship caused by mutations in transcription factors is still difficult to predict and may cause unwanted side effects on other commercially important properties. Genetic engineering of metabolic pathways in industrial microorganisms is clearly limited by a lack of knowledge on regulatory factors and their mechanisms of action. This is particularly true under the conditions occurring in industrial applications. A promising strategy to fill this gap is reverse engineering of genes identified by genetic analysis of natural and industrial strains with interesting traits (Bailey et al., 1996). Most of these traits, however, are complex and only recently methodologies have become available for efficient mapping and identification of the multiple mutant genes responsible for such complex traits (Swinnen et al., 2012b).

The exceptional capacity of the yeast *Saccharomyces cerevisiae* for anaerobic production of ethanol is the basis of nearly all industrial production of alcoholic beverages and fuel ethanol. Apart from carbon dioxide, glycerol is the most important byproduct in yeast ethanolic fermentation. Under anaerobic conditions, glycerol production is closely connected to the growth rate of the cells. The withdrawal of intermediates from glycolysis for biosynthetic purposes necessitates regeneration of NAD+ to sustain the redox balance and in the absence of oxygen. This is accomplished by formation of glycerol (Bakker et al., 2001). A second function for glycerol production in yeast is its use as a compatible osmolyte under conditions of hyperosmotic stress (Blomberg and Adler, 1989; Hohmann, 2002).

Glycerol is synthesized in two steps from dihydroxyacetone phosphate by NAD+ dependent glycerol-3-phosphate dehydrogenase (GPDH) and glycerol-3-phosphate phosphatase, encoded by GPD1 and GPD2, and GPP1 and GPP2, respectively, (Albertyn et al., 1994; Ansell et al., 1997). Enhanced expression of GPD1 is a major factor responsible for stimulation of glycerol production under osmostress (Albertyn et al., 1994; Larsson et al., 1993; Nevoigt and Stahl, 1997). The high osmolarity glycerol (HOG) pathway, responsible for osmostress-induced glycerol production and other cellular adaptations, has been characterized in great detail (Brewster et al., 1993; Hohmann, 2002). Changes in extracellular osmolarity are sensed via two independent sensors, Sho1 and Sln1, that both activate the HOG Map kinase pathway. The Sln1 branch plays the most prominent role and acts through a phosphotransfer system, composed of Sln1, Ypd1 and Ssk1. The two pathways converge on the phosphorylation of Pbs2, which activates the Map kinase Hog1. This causes translocation of Hog1 into the nucleus, where it activates several transcriptional regulators, i.a., Sko1, Msn2, Smp1 and Hot1. These regulators induce GPD1 expression to enhance the formation of glycerol under osmostress (Hohmann, 2002). Retention of glycerol within the cells and its efflux upon relief of osmostress are controlled by the Fps1 plasma membrane channel (Luyten et al., 1995).

Engineering of glycerol production in yeast has attracted considerable attention. Higher glycerol levels are desirable in wine and beer production as well as industrial glycerol production (Cambon et al., 2006; Geertman et al., 2006; Heux et al., 2006; Nevoigt and Stahl, 1996; Remize et al., 1999; Schuller and Casal, 2005). Multiple genetic modifications have been used to raise glycerol production and counteract the side effect of higher acetate production (Cambon et al., 2006; Eglinton et al., 2002; Ehsani et al., 2009). Lower glycerol levels are highly desirable in ethanol fuel production because they are usually associated with increased ethanol yields (Basso et al., 2008; Bro et al., 2006; Nissen et al., 2000a; Nissen et al., 2000b). High ethanol yield is a key characteristic of bioethanol production strains, reaching approximately 90-93% of the theoretical maximum of 0.51 g ethanol per g glucose in current industrial processes (Bai et al., 2008). Despite the high ethanol yield, part of the sugar is still used for yeast growth and glycerol production. Glycerol yield can reach up to 2.0-3.6 g per 100 g consumed glucose as already reported by Pasteur (Pasteur, 1858). Glycerol yields strongly depend on fermentation conditions (Alfenore et al., 2004; Bideaux et al., 2006; Gardner et al., 1993) and medium composition, especially the type of nitrogen source used (Albers et al., 1996). A key challenge in industrial ethanol production is lowering glycerol yield without compromising osmostress tolerance and growth rate under anaerobic conditions.

Osmotolerance is an important trait for industrial production, storage and utilization of yeast and growth rate is closely correlated with ethanol production rate under anaerobic conditions. Hence, diminution of GPD1 and/or GPD2 expression is not an option since it likely compromises osmostress tolerance and growth under anaerobic conditions (Ansell et al., 1997; Bjorkqvist et al., 1997; Nissen et al., 2000a). Even strains with fine-tuned reduction in GPDH activity obtained with promoter engineering still showed a significant drop in osmotolerance and/or growth rate resulting in lower ethanol productivity (Hubmann et al., 2011; Pagliardini et al., 2010). Hence, traditional rational metabolic engineering of glycerol production using modification of structural, enzyme-encoding pathway genes has so far led to little success for practical application. Reverse metabolic engineering is an attractive alternative (Bailey et al., 1996), but the identification of the genetic basis of complex traits, such as glycerol yield in fermentation, has remained for many years an important bottleneck. The availability of genome-wide methods for scoring SNPs as genetic markers has facilitated simultaneous mapping of multiple linked loci referred to as quantitative trait loci (QTLs) (Brem et al., 2002; Deutschbauer and Davis, 2005; Steinmetz et al., 2002; Winzeler et al., 1998). Next generation sequencing methods now allow very efficient QTL mapping using whole-genome sequence analysis of pooled segregants displaying the trait of interest (Ehrenreich et al., 2010; Parts et al., 2011; Swinnen et al., 2012a). In most proof-of-principle fundamental studies on QTL analysis traits are studied that can be scored easily in large numbers, i.e., thousands, of segregants. Many traits of industrial importance, however, are much more cumbersome to score, requiring, for instance, several individual small-scale fermentations per segregant. An important issue, therefore, in genetic analysis of complex traits of industrial importance is the minimum number of segregants required for successful identification of QTLs and causative genes.

Using a pooled-segregant whole-genome sequence analysis approach for identification of genetic elements determining glycerol yield in yeast fermentation, we surprisingly identified a mutant SSK1 allele as the causative allele for low glycerol production. Introduction of the mutant SSK1 allele in the industrial target strain significantly lowered the glycerol/ethanol ratio without compromising osmotolerance or ethanol productivity. Even more surprisingly, deletion of SSK1 caused a less pronounced effect, indicating a specific role of the truncated ssk1 protein in lowering glycerol production.

A first aspect of the disclosure is an isolated truncated yeast ssk1 protein. The yeast ssk1 protein is known to the person skilled in the art, and is represented in SEQ ID NO:2. A "truncated ssk1 protein," as used herein, means that a part of the wild-type carboxy terminal protein is missing. Preferably, at least the response regulator receiver domain (amino acid 507-636) is deleted in the truncated protein. Preferably, the truncated protein comprises at least the 50 amino terminal amino acids, more preferably at least the 100 amino terminal amino acids, even more preferably at least the 150 amino terminal amino acids, even more preferably at least the 200 amino terminal amino acids, even more preferably at least the 250 amino terminal amino acids, most preferably at least the 300 amino terminal amino acids of SEQ ID NO:2. As a non-limiting example, the truncated protein may be created by a point mutation introducing of a stop coding in the reading frame of SEQ ID NO:1, or by a deletion or insertion resulting in a stop coding. In the latter case, the deletion or insertion may cause a frame shift, resulting in a mutant sequence at the carboxy terminal end of the truncated protein. Preferably, the mutant sequence comprises, even more preferably consist of amino acid 330-356 of SEQ ID NO:4. Alternatively, the truncated protein, according to the disclosure, is a fusion protein, wherein the amino terminal end of the ssk1 protein is fused to another polypeptide. In a preferred embodiment, the truncated protein is encoded by a nucleic acid comprising SEQ ID NO:3.

A second aspect of the disclosure is a gene, encoding a truncated protein, according to the disclosure. In a preferred embodiment, the gene is encoded by a nucleic acid comprising SEQ ID NO:3.

Another aspect of the disclosure is the use of a truncated ssk1 protein, according to the disclosure, to limit glycerol production in yeast. "To limit glycerol production," as used herein, means that the glycerol production of the strain, comprising the truncated ssk1 protein, is lower than that of a strain with wild-type ssk1 protein, and lower than that of a strain with a full deletion of the SSK1 gene, when used under the same fermentation conditions. Preferably, the glycerol production is lower than 0.06 g $g^{-1}$, when tested on minimal medium with 5% glucose.

Yeast, as used herein, can be any yeast useful for ethanol production, including, but not limited to, *Saccharomyces, Zygosaccharomyces, Brettanomyces* and *Kluyveromyces*. Preferably, the yeast is a *Saccharomyces* sp., even more preferably it is a *Saccharomyces cerevisiae* sp.

Preferably, the truncated ssk1 protein is combined with one or more mutant alleles encoding proteins further limiting the glycerol production. Even more preferably, the alleles are encoding proteins selected from the group consisting of gpd1$^{L164P}$, hot1$^{P107S,H274Y}$ and smp1$^{R110Q,P269Q}$, most preferably a protein selected from the group consisting of SEQ ID NO:5, SEQ ID NO:6 and SEQ ID NO:7.

Another aspect of the disclosure is a recombinant yeast strain, comprising a gene encoding a truncated ssk1 protein, according to the disclosure. Preferably, the gene is replacing the wild-type gene, as a result of transformation and homologous recombination. In case of a diploid, polyploidy or aneuploidy strain, one or more wild-type copies may be replaced by the gene encoding the truncated protein; preferably, all wild-type copies have been replaced by the gene encoding the truncated protein. Even more preferably, the gene is combined with another gene further limiting the glycerol production. More preferably, the gene is an allele encoding a protein selected from the group consisting of gpd1$^{L164P}$, hot1$^{P107S,H274Y}$ and smp1$^{R110Q,P269Q}$, most preferably a protein selectee from the group consisting of SEQ ID NO:5, SEQ ID NO:6 and SEQ ID NO:7. Preferably, the yeast is a *Saccharomyces* sp., even more preferably it is a *Saccharomyces cerevisiae* sp.

Still another aspect of the disclosure is the use of a recombinant yeast strain, according to the disclosure, for high-yield ethanol production. "High-yield ethanol production," as used herein, means an ethanol production wherein the byproducts, especially glycerol are limited, giving a low ratio of glycerol over ethanol. Preferably, the glycerol over ethanol ration is lower than 4%, even more preferably lower than 3.75%. Most preferably, the ratio is 50% lower than the ration of the strain carrying the wild-type SSK1 alleles. Alternatively, the wild-type SSK1 allele can be used, preferably in combination with wild-type GDP1, HOT1 and/or SMP1 alleles to obtain a yeast strain with high glycerol production and limited alcohol production. Such strain may be useful, as a non-limiting example, as a wine yeast in regions with a high average temperature, in order to limit the alcohol content of the wine.

Another aspect of the disclosure is a method for isolating a high ethanol yield yeast strain, preferably a low glycerol producing strain as defined above, comprising analysis of the SSK1 gene. Indeed, apart from introducing a gene encoding a truncated ssk1 protein by transformation, one can obtain a similar result by mutagenesis, or by crossing a strain with a mutant strain carrying the mutant ssk1 allele, and extensive analysis of the mutants of descendants, to screen for strain comprising a gene encoding a mutated ssk1 protein. Such screening can be done, as a non-limiting example, at nucleic acid level, by hybridization or by sequence analysis, or by ELISA analysis, using an antibody specific for the missing carboxyterminal end. Therefore, another aspect of the disclosure is the use of the analysis of the SSK1 gene and/or the SSK1 protein for the selection of a high ethanol yield yeast strain, preferably a low glycerol producing strain as defined above. Preferably, the yeast is a *Saccharomyces* sp., even more preferably it is a *Saccharomyces cerevisiae* sp.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 7A) Glycerol and ethanol yields in fermentations with minimal medium (5% wv glucose), high gravity medium (YP with 33% wv glucose) and wheat hydrolyzate (SHF: Separate Hydrolysis and Fermentation). (FIGS. 7B and 7C) Glycerolethanol ratio and maximal volumetric ethanol production rate (rmax in g 1-1 h-1) in fermentations with minimal medium (5% glucose) in the presence of NaCl (0, 0.7 and 1.4M) or sorbitol (0, 1.4 and 2M).

DETAILED DESCRIPTION

EXAMPLES

Materials and Methods to the Examples

Microbial Strains and Cultivation Conditions

Figure 1:
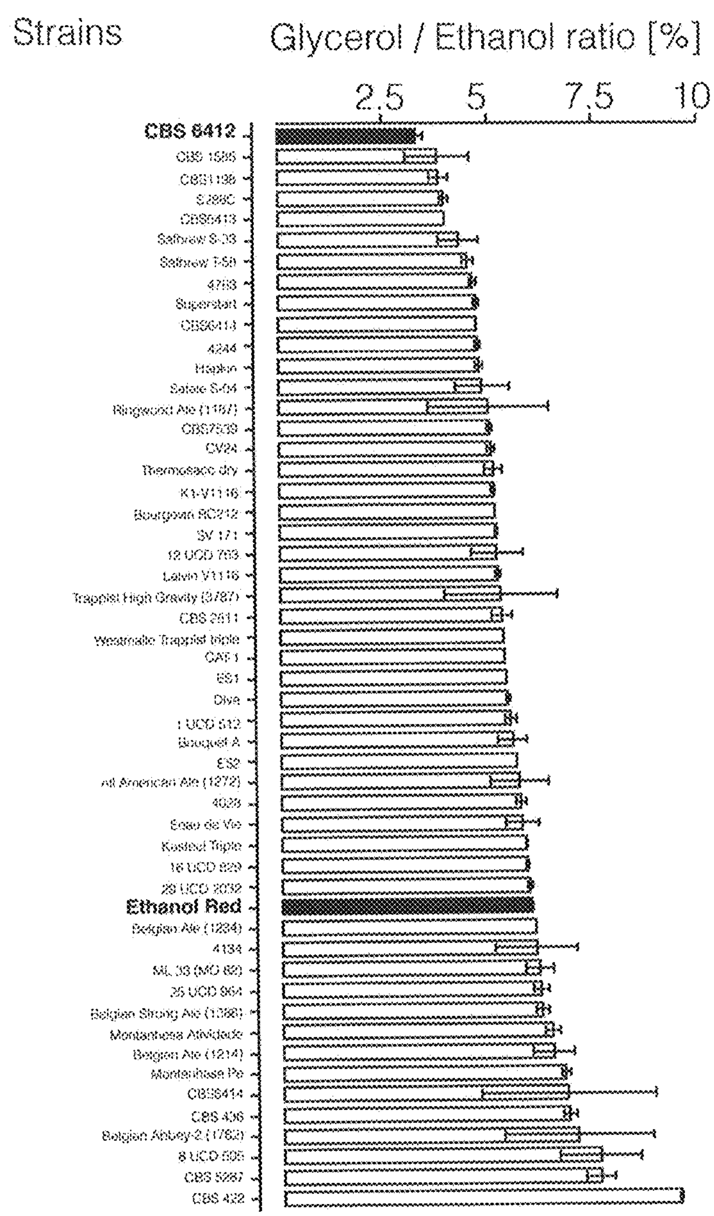
FIG. 1: Variation in glycerol and ethanol yield. (A) Glycerol/ethanol ratio in 52 natural and industrial *S. cerevisiae* strains. The selected diploids used for quantitative trait analysis, Ethanol Red (inferior parent, target industrial bioethanol production strain) and CBS6412 (superior parent) are marked in black. (B) Normal distribution of the glycerol/ethanol ratio around a mean value of 5.7% for the 52 strains.
Figure 1:
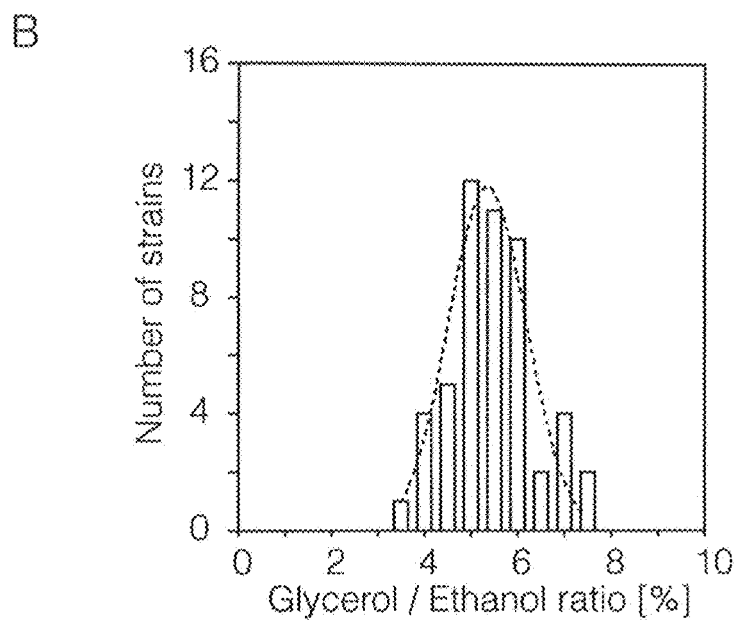

All *S. cerevisiae* strains used are listed in Table 1. Strain CBS6412 was originally indicated as sake yeast Kyokai No. 7 in the CBS collection, but comparison of the genome sequence revealed that this indication was erroneous. *E. coli* strain DH5αTM (Invitrogen Corp., Carlsbad) was used for amplification of plasmids. The strain was grown in Luria-Bertani (LB) medium containing 0.5% wv yeast extract, 1% wv Bacto tryptone, 1% wv NaCl, (pH 7.5) at 37° C. *E. coli* transformation and isolation of plasmid DNA was carried out using standard techniques (Sambrook et al., 1989).

Transformants were selected on LB medium containing 100 μg/ml ampicillin.

Mating, Sporulation and Tetrad Analysis

Mating, sporulation and dissection of asci were carried out according to standard procedures (Sherman and Hicks, 1991). Mating type of segregants was determined by diagnostic PCR for the MAT locus (Huxley et al., 1990).

Fermentation Conditions

A selection of 52 *S. cerevisiae* wild-type strains was screened in 250 ml oxygen limited and stirred fermentations containing 1% wv yeast extract, 2% wv peptone and 12% wv glucose. Screening of the selected parent strains and the segregants was performed in 15 ml falcon tubes containing 5 ml minimal medium containing 1.9 g 1-1 yeast nitrogen base (Difco), 5 g 1-1 ammonium sulphate, 250 mg 1-1 leucine, 50 mg 1-1 uracil, 100 mg 1-1 histidine, 30 mg 1-1 lysine, 20 mg 1-1 methionine and 50 g 1-1 glucose. Fermentations were inoculated with an initial OD of 1 and their progress followed by weight loss. Selected segregants were also tested in 100 ml oxygen-limited stirred fermentations. All fermentations were carried out at 30° C.

High gravity fermentations were carried out in fermentation tubes containing 250 ml of YP and 33% wv glucose. Precultures used as inoculum were first grown on YP 2% wv glucose for 24 hours and then on YP 10% wv glucose up to an OD600 of 1. The fermentations were inoculated with 5.107 cells/ml and kept at 25° C. Stirring was applied for the first 4 h (120 rpm). When the weight loss was stable for 2 consecutive days, the fermentation was considered to be finished.

SHF (Separate Hydrolysis and Fermentation) fermentations were carried out with wheat liquefact (24.5% dry mass content) acquired from a local ethanol plant. After adjustment of the pH to 4.5 with sulfuric acid, it was treated with DEXTROZYME® (Novozyme, Denmark) for 24 h at 60° C. to obtain hydrolysate. The latter was boiled at 100° C. for 20 min and then cooled. Oxygen-limited fermentations were carried out with 100 ml of this medium inoculated with 5 ml of yeast suspension. The fermentations were performed at 30° C. and were continuously stirred at 200 rpm.

Assessment of osmotolerance was performed in fermentations containing minimal medium with or without 0.7M or 1.4M NaCl, or 1M or 2M sorbitol. The fermentations were continuously stirred at 200 rpm.

Determination of Fermentation Parameters

In all fermentations weight loss was used to follow the progress of the fermentation. Glucose, glycerol and ethanol in the medium were determined by HPLC (WATERS® isocratic BREEZE™ HPLC, ion exchange column WAT010290). Column temperature was 75° C., 5 mM H2SO4 was used as eluent with a flow rate of 1 ml min-1 and refractive index detection was used (Waters, 2414 RI detector). Biomass was determined by OD600 at the beginning and the end of fermentation and yeast dry mass also at the end. The product yield was calculated from the final product concentration (g. 1-1) and the difference in glucose concentration at the start and end of fermentation (consumed glucose in g. 1-1). The product yields in the SSF were based on the final product concentrations and the equivalent initial glucose concentration (the latter was measured in a completely hydrolyzed sample of wheat liquefact).

DNA Methods

Yeast genomic DNA was extracted with Phenol/Chloroform/Isoamyl-alcohol (25:24:1) (Hoffman and Winston, 1987) and further purified with diethyl-ether extraction or ethanol precipitation if required. PCR was performed with high-fidelity polymerases PHUSION® (Finnzymes) or ExTAQ™ (TaKaRa) for cloning, amplification of deletion or insertion cassettes, and sequencing purposes. Sequencing was carried out using the dideoxy chain-termination method (Sanger and Coulson, 1975) at the VIB Genetic Service Facility (Antwerp). The sequences were analyzed with geneious (Geneious Basic 5.3.4), SEQMAN® (Lasergene Coresuite 8) or CLC DNA workbench (CLC bio) software.

Pooled-Segregant Whole-Genome Sequence Analysis

After crossing the two parent strains CBS4C and ER7A, the 20 most superior segregants (lowest glycerol production) were assembled in the "selected pool" while 20 random segregants were used to assemble the "unselected pool." The two pools were made by combining equal amounts of cells based on OD600. High molecular weight DNA (3 μg, ~20 kb fragments) was isolated from the pools and parent strains according to Johnston and Aust (1994). The purity of the DNA sample was estimated from UV measurement (260280=1.7-2.0). The DNA samples were provided to GATC Biotech AG (Konstanz, Germany) and BGI (Hong Kong, China) for whole genome sequence analysis by Illumina technology. QTL analysis based on the distribution of SNP variant frequency over the length of the chromosomes was carried out as described by Swinnen et al., (2012a). The short read sequences obtained from the parental strains and the pools were mapped against the known S288c reference sequence using the mapping software Bfast (Homer et al., 2009). After pairing, unique alignments for the CBS4C strain were selected and homozygous variants, i.e., SNPs and small indels, were called using SNVQ (Duitama et al., 2012). In addition, regions with coverage below 0.5 or above 1.5 of the average coverage were identified and SNPs of those regions were filtered out. For each polymorphic position the variant calls in the aligned reads for the ER7A strain were then extracted and variants were filtered out for which the coverage of the reference variant was too small (<20×) or too large (>150×) or SNPs of both parents coincided but were different from the reference. Finally, the number of calls to the reference and the alternative variant of each selected polymorphic position was determined from the set of aligned reads corresponding with the segregant pools. The SNP variant frequencies were calculated by dividing the number of the alternative variant by the total number of aligned reads. A very high or a very low frequency was a sign of a one-sided SNP segregation preferentially coming from one parent, indicating a genetic linkage to the trait of interest. Genetic linkage was statistically confirmed using the methods described earlier (Swinnen et al., 2012a).

Detection of SNP Markers

Individual SNPs were scored by PCR. The forward and reverse primer contained the nucleotide of ER7A or CBS4C as the 3' terminal nucleotide. The annealing temperature was optimized using DNA extracts of ER7A and CBS4C so as to allow only hybridization with primers containing a complete match.

Reciprocal Hemizygosity Analysis (RHA)

For RHA analysis (Steinmetz et al., 2002), two diploid strains were constructed by crossing CBS4C and ER7A wild-type or ssk1Δ strains, so that the resulting diploids only contained a single SSK1 allele, either CBS4C derived $ssk1^{E330N \ldots K356N}$ or ER7A derived SSK1. Deletion cassettes were constructed essentially as described by Gueldner et al., (2002) with the phleomycin resistance marker bleR and SSK1 gene deletion was confirmed by PCR. The selection marker was removed using the CreloxP system. The removal of the selection marker was verified by phleomycin sensitivity as well as by PCR. RHA was performed with three independent isolates of all tested diploids.

Construction of SSK1 Insertion Cassettes

The repeat region H1 was PCR amplified with the primers A-6101 and A-6103 using genomic DNA of CBS4C and ER7A as template. The resulting PCR fragment was digested with KpnI and SalI and purified from an agarose gel. SSK1 was PCR amplified from genomic DNA of CBS4C and ER7A and the primers A-6100 and A27 6102. The obtained product of around 2800bp was digested with SalI and XmaI. The cloning vector pBluescriptII SK(+) (Fermentas) was digested with KpnI and XmaI and ligated with the repeat region H1 and the SSK1 allele of the respective strain. The construct was verified using Sanger sequencing. The two selectable and counter-selectable systems, AMD1 and NAT1-GIN11, were used to introduce the insertion cassette. During counter-selection, the marker genes spontaneously looped out via the H1 repeat region, leaving no scars of non-*S. cerevisiae* DNA in the genome. The AMD1 marker of *Zygosaccharomyces rouxii* was cut out of the plasmid pF6a-

AMD1-MX6 using SacI and BglII (Shepherd and Piper, 2010). The fragment was gel purified and ligated with pUG66, which was also digested with the same two enzymes. The resulting plasmid pUG-AMD was used for PCR amplification of the AMD1 marker using the primers A-5166 and A-6770. The PCR product as well as the H1-SSK1 plasmids were digested with SalI and ligated, resulting in plasmids pBluescriptII_AMD1_ ssk1$^{E330N \ldots K356N}$ and pBluescriptII_AMD1_SSK1. The selection marker NAT1 was amplified from pAG25 using primers A-7116 and A-7117. The GIN11 counter-selection marker (Akada et al., 2002) was amplified from pG119 using primers A-7118 and A-7119. Both fragments were sequentially digested with DraIII and SalI and ligated with the H1-SSK1 plasmid, which was previously digested with SalI resulting in the plasmids pBluescriptII_NAT1_ GIN11_ssk1$^{E330N \ldots K356N}$ and pBluescriptII_ NAT1_GIN11_SSK1. The insertion cassette H1-loxP-AMD1-loxP-SSK1 and H1-loxP-AMD-loxP-ssk1$^{E330N \ldots K356N}$ were amplified from pBluescriptII_ AMD1_SSK1 and pBluescriptII_AMD1_ssk1$^{E330N \ldots K356N}$ using the outside flanking primers matching the M13 primer binding sites of the plasmid pBluescriptII SK(+). The PCR product was purified and used for transformation. Cassettes with H1-NAT1-GIN11-SSK or H1-NAT1-GIN11_ ssk1$^{E330N \ldots K356N}$ were digested with BspHI and digestion products were used for transformation. Yeast was transformed with the LiAc/PEG method (Gietz et al., 1992).

Reciprocal SSK1 Allele Replacement in CBS4C and ER7A

Site-directed modification of the CBS4C and ER7A SSK1 locus was carried out using a two step-method. In the first step, the SSK1 insertion cassettes (see above) were transferred to the SSK1 deletion strains, CBS4C ssk1Δ and ER7A ssk14. After transformation, positive clones were selected on YD agar plates containing 200 μg/ml ClonNat. The presence of the insertion cassette was verified by PCR using the primers A-5168 and A-7301 o In the second step, the marker genes were removed by selection of spontaneous loop-outs on galactose-containing medium after induction of the counter-selectable marker GIN11 (Akada et al., 2002; Akada et al., 1999; Olesen et al., 2000). Positive looped-out clones were identified by ClonNat sensitivity and verified by PCR using the forward primer A-5168 and the SSK1 allele specific reverse primers A-5126 and A-5127. The inserted SSK1 alleles were verified by Sanger sequencing.

SSK1 Allele Replacement in the Industrial Strain Ethanol Red

The ssk1$^{E330N \ldots K356N}$ allele of CBS4C was inserted twice in the Ethanol Red derivative, HG5 (see Table 1), which had both SSK1 alleles deleted. The latter strain was constructed by introducing a disruption cassette flanked with loxP sites using homologous recombination (Gueldener et al., 2002; Kotaka et al., 2009). The disruption cassette was constructed with homologous sequences (H1/H2) corresponding to the 5' and 3' end of the SSK1 ORF surrounding the phleomycin resistance-gene bleR used as selectable marker. The selectable marker, bleR, was removed by Cre recombinase. A second disruption cassette was constructed with the recombination sites H1* and H2*, which were located inside the first homologous integration sites, H1 and H2, enabling specific recombination into the 2nd SSK1 allele of the diploid strain. Gene disruption was verified by PCR. The bleR marker gene was again removed using the CreloxP system. The double deletion was confirmed by PCR using primers located outside the integration site. The two ssk1$^{E330N \ldots K356N}$ insertion cassettes, H1-loxP-AMD1-loxP-ssk1$^{E330N \ldots K356N}$ and H1-NAT1-GIN11-ssk1$^{E330N \ldots K356N}$, were successively transformed. After the 1$^{st}$ transformation of the H1-loxP-AMD1-loxP-ssk1$^{E330N \ldots K356N}$ cassette, transformants were selected based on hydrolysis by Amd1 of acetamide used as sole nitrogen source. The correct integration of the insertion cassette was verified by PCR using the primers A-5168 and A-5894 inside the AMD gene. In the 2nd transformation, the H1-NAT1-GIN11-ssk1$^{E330N \ldots K356N}$ was transferred. Positive transformants were selected on acetamide medium, containing 200 μg/ml ClonNat. Correct integration in the 2$^{nd}$ chromosome was verified by PCR using the primers A-5168 and A-7301 to test the presence of the insertion cassette as well as the primers A-5168 and A-5169 to verify the disappearance of the two ORF deletions of the Ethanol Red ssk1Δ/Δ. Counter-selection was simultaneously applied for both marker systems using medium with 100 mM fluoroacetamide and 0.04% galactose (induction of GIN11).

Example 1

Selection of Parent Strains for Genetic Mapping of Low Glycerol Yield

We have evaluated 52 diploid *S. cerevisiae* strains from diverse origins for the ratio between the amount of glycerol and ethanol produced in small-scale (250 ml) fermentations with complex medium containing 12% glucose. A continuous and normal distribution of the trait was observed (FIG. 1). The CBS6412 strain showed the lowest glycerol yield (0.043 g. g-1) of all strains tested, which was about 63% of that of the reference industrial strain Ethanol Red (0.068 g. g-1) (FIG. 2A), an industrial strain commonly used for bioethanol production with corn and wheat starch hydrolysate. As it had both a low glycerol/ethanol ratio and a low glycerol yield, CBS6412 was chosen as the superior strain and Ethanol Red was used as the inferior strain. In order to obtain haploid strains for genetic mapping analysis, the two diploid strains were sporulated and segregants were tested in small-scale fermentations. Glycerol yields of the segregants were normally distributed around those of the diploid parents (FIG. 2B), indicating a highly heritable phenotype. The CBS6412 segregant, CBS4C, had an even lower glycerol yield than its parental diploid (FIG. 2A), indicating acquirement of one or more beneficial, recessive alleles present in heterozygous form in the diploid strain. CBS4C was selected as the superior parent strain for the genetic mapping. The Ethanol Red segregant ER7A had a glycerol yield closest to its parental diploid and served as inferior parent strain.

Example 2

Figure 2:
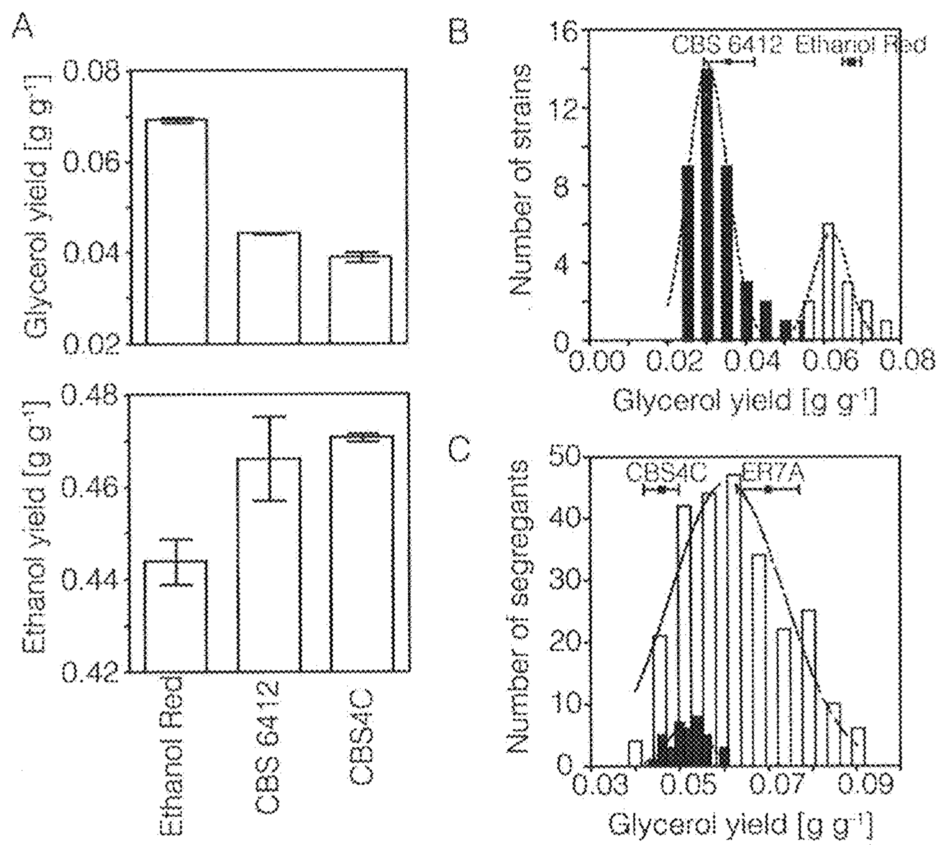
FIG. 2: Glycerol and ethanol yield in the segregants of the diploid parent strains and in segregants from the cross between the selected haploid parent strains. (A) Glycerol and ethanol yield of the diploids, Ethanol Red and CBS6412, and the CBS6412 segregant, CBS4C, showing the lowest glycerol yield of all tested segregants of CBS6412. Fermentations were carried out in 100 ml minimal medium with 10% glucose. (B) Distribution of the glycerol yield in the haploid segregants of CBS6412 (black bars) and Ethanol Red (white bars). The distribution was normal around the value of the diploid parents, CBS6412 (left small black square on top) and Ethanol Red (right small black square on top). (C) Distribution of the glycerol yield in the segregants from the cross CBS4C×ER7A (white bars). All segregants were screened in 5 ml fermentations. After evaluation of the 48 segregants with the lowest glycerol yield in 100 ml minimal medium with 5% glucose, the 44 segregants with the lowest glycerol production were selected for pooled-segregant whole-genome sequence analysis (black bars). The glycerol yield of the haploid parents CBS4C and ER7A is indicated with small black squares on top.
Figure 3:
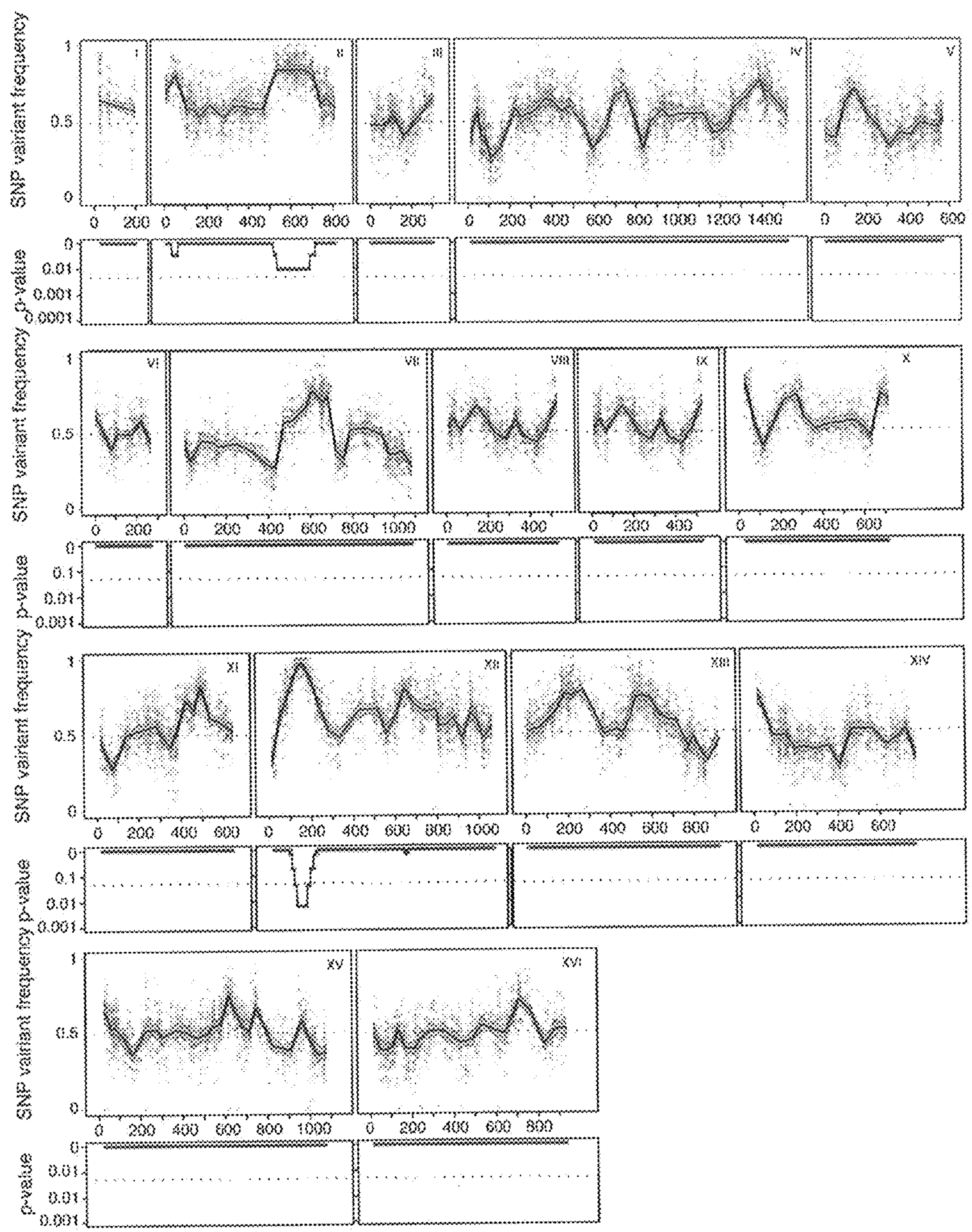
FIG. 3: Plots of SNP variant frequency versus chromosomal position and corresponding P-values. The variation in SNP variant frequency is shown for all 16 yeast chromosomes (raw data: small grey circles; smoothened data: black line; statistical confidence interval: grey lines). Significant upward deviations from the average of 0.5 indicate linkage to the superior parent CBS4C, while significant downward deviations indicate linkage to the inferior parent ER7A. The smoothened line was determined as described previously (Swinnen et al., 2012a). Strong candidate QTLs were found on chromosome II (at position 500,000-700,000 bp) and chromosome XII (at position 135,000-200,000 bp), but only for the latter the P-value dropped below the significance limit of 0.05.
Figure 4:
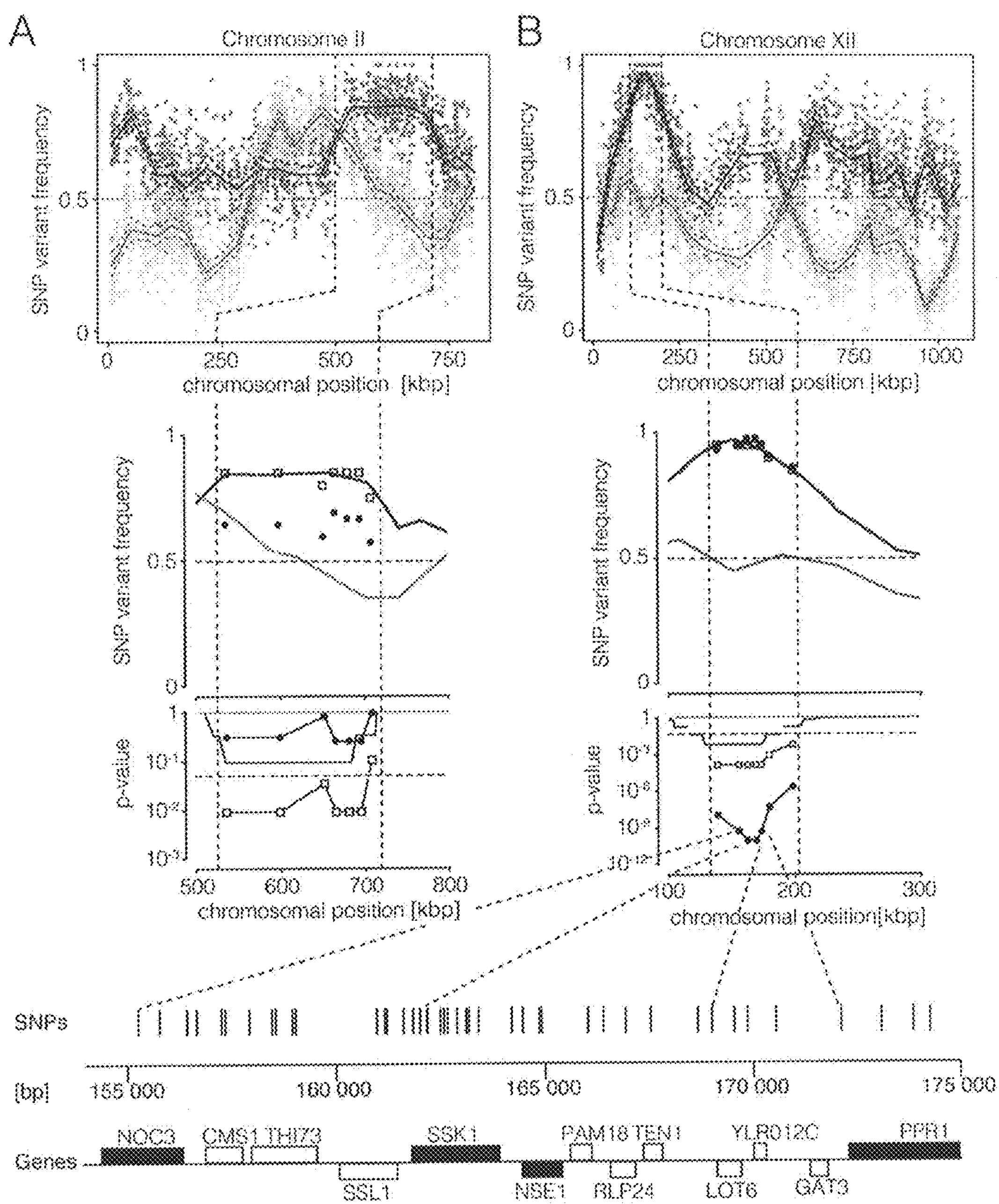
FIG. 4: SNP variant frequency and P-values determined in individual segregants for downscaling of the QTLs. Top: SNP variant frequency map of chromosome II (A) and chromosome XII (B) determined with the pool of 20 selected segregants (raw data: small circles; smoothened data: black line; statistical confidence interval: black stippled lines) and the pool of 20 unselected segregants (raw data: small triangles; smoothened data: grey line; statistical confidence interval: grey stippled lines). Middle: SNP variant frequency of seven selected SNPs in the candidate regions on chromosome II (at position 500,000-700,000 bp) (A) and chromosome XII (at position 135,000-200,000 bp) (B), determined in the individual 20 most superior segregants (□) and the individual 44 most superior segregants (●). Smoothened lines: SNP variant frequency determined with the pool of 20 selected segregants (black line) and the pool of 20 unselected segregants (grey line). Bottom: P-values for the same seven SNPs in the regions on chromosome II (A) and XII (B). The statistical confidence line (P-value≤0.05) is also indicated. The region on chromosome XII was significantly linked. Lowest panel: overview of all genes present and all SNPs identified in the region with the highest linkage of the QTL on chromosome XII (154,000 bp-175,000 bp). Genes marked with a star contained a non-synonymous mutation in the ORF.

Construction of the CBS4C/ER7A Hybrid and Selection of Superior Segregants with Low Glycerol Yield The CBS4C and ER7A haploid strains were crossed with each other and 257 segregants were isolated and first characterized for glycerol and ethanol yield in 5 ml fermentations with 5% glucose in minimal medium. FIG. 2C shows a histogram of the glycerol yield in the segregant population in comparison with that of the CBS4C and ER7A haploid parents. The glycerol yield showed a normal distribution and most segregants had a glycerol yield close to the average (0.063 g. g-1, ±142% of the CBS4C glycerol yield). We re-tested the 48 segregants with a glycerol yield below 120% of the CBS4C parent in 100 ml small-scale fermentations; 44 segregants showed the same low glycerol yield also under these conditions. Among these, the 20 segregants showing the lowest glycerol yield (≤0.054 g g-1) were selected for QTL mapping with pooled-segregant whole-genome sequence analysis. The 24 remaining segregants were used for subsequent validation of the results as described below. A second pool with 20 randomly selected segregants was also subjected to pooled-segregant whole-genome sequence analysis and used as control. QTL mapping using pooled-segregant whole-genome sequence analysis. The genomic DNA of the selected and random pools, as well as the two parent strains, was extracted and submitted to custom sequence analysis using Illumina HiSeq 2000 technology (GATC Biotech AG, Konstanz, Germany; BGI, Hong Kong, China). The sequence reads of the CBS4C and ER7A parent strains were aligned with the S288c standard sequence, which allowed to identify 21,818 SNPs between CBS4C and ER7A. The SNPs were filtered as described previously (Duitama et al., 2012). The variant frequency of the quality-selected SNPs in the DNA of the two pools was then plotted against the SNP position on the chromosome. The scattered raw data were smoothened by fitting smoothing splines in the generalized linear mixed model framework as previously described (Swinnen et al., 2012a). The results are shown in FIG. 3. A prominent QTL with strong linkage was present on chromosome XII (between 135,000 and 200,000 bp) and is shown in more detail in FIG. 4B. Individual SNPs from that region, as well as from the QTL with lower linkage on chromosome II (FIG. 4A), were scored by PCR detection in the 20 individual segregants of the selected pool (FIGS. 4A and 4B). The precise SNP variant frequency determined in this way was used to verify the linkage of the two regions on chromosome II and XII, respectively. This revealed a very strong linkage with low glycerol yield for the QTL on chromosome XII with the minimal P-value being 1.45.10-4, while the P-values for the QTL on chromosome II only dropped just below the 0.05 threshold for significance (0.009). The same SNPs were also scored in the 24 remaining segregants with a glycerol yield below 120% of the CBS4C parent. Calculation of the P-values for the whole group of 44 segregants no longer revealed significant linkage for the QTL on chromosome II. On the other hand, the P-values for the QTL on chromosome XII dropped to 9.10-11, strongly increasing significance of the linkage. Hence, we concentrated the further analysis on the QTL of chromosome XII.

Example 3

Identification of SSK1 as a Causative Gene in the QTL on Chromosome XII

Figure 5:
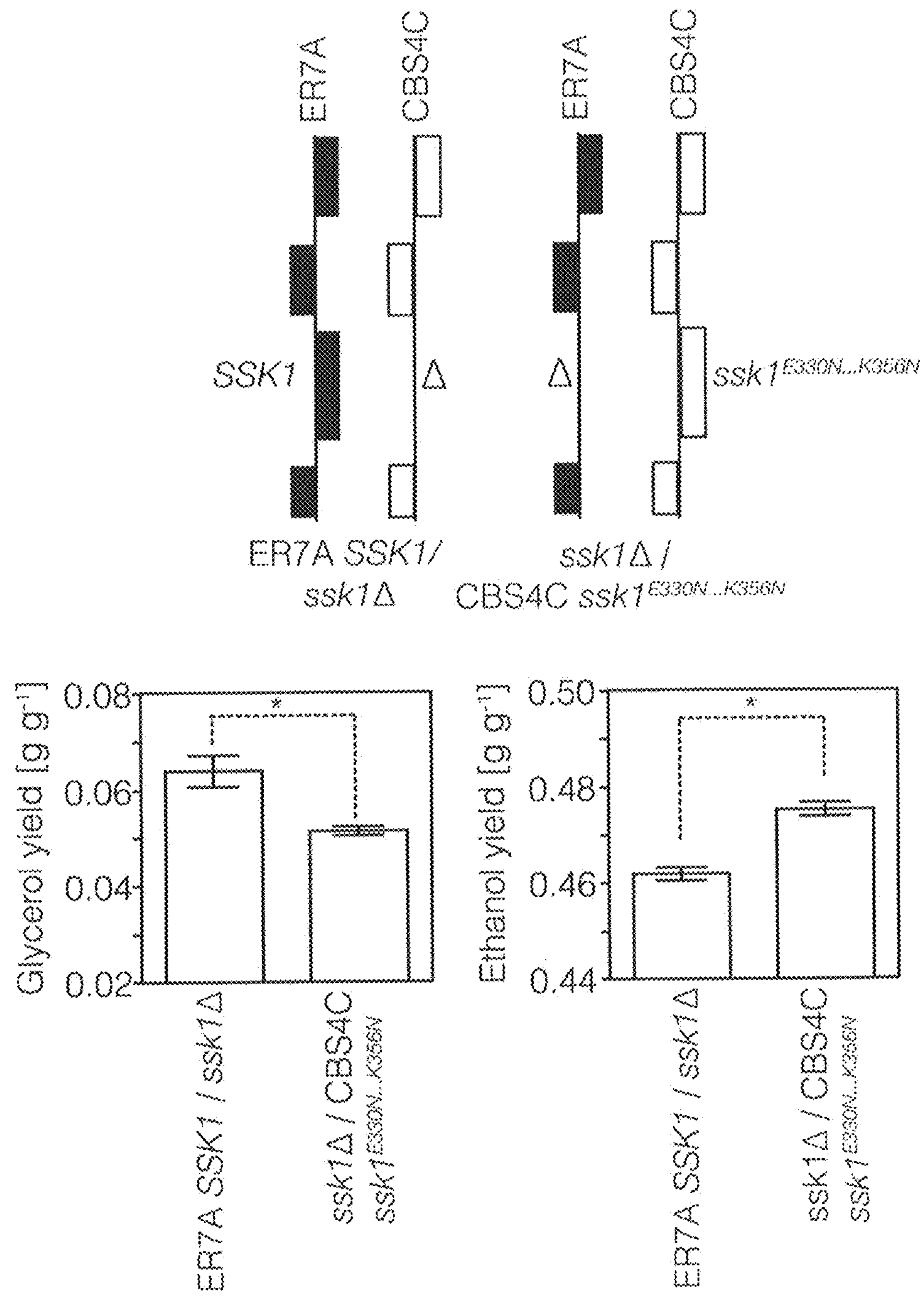
FIG. 5: Identification of SSK1 as the causative gene in the QTL on chromosome XII. Diploid strains constructed for reciprocal hemizygosity analysis (RHA) with either the deletion of the ssk1$^{E330N \ldots K356N}$ allele of CBS4C or the deletion of the SSK1 allele of ER7A. Glycerol and ethanol yield of the two hemizygous diploid strains. The difference in glycerol and ethanol yield for the two diploids was significant by the Student t-test.
Figure 6:
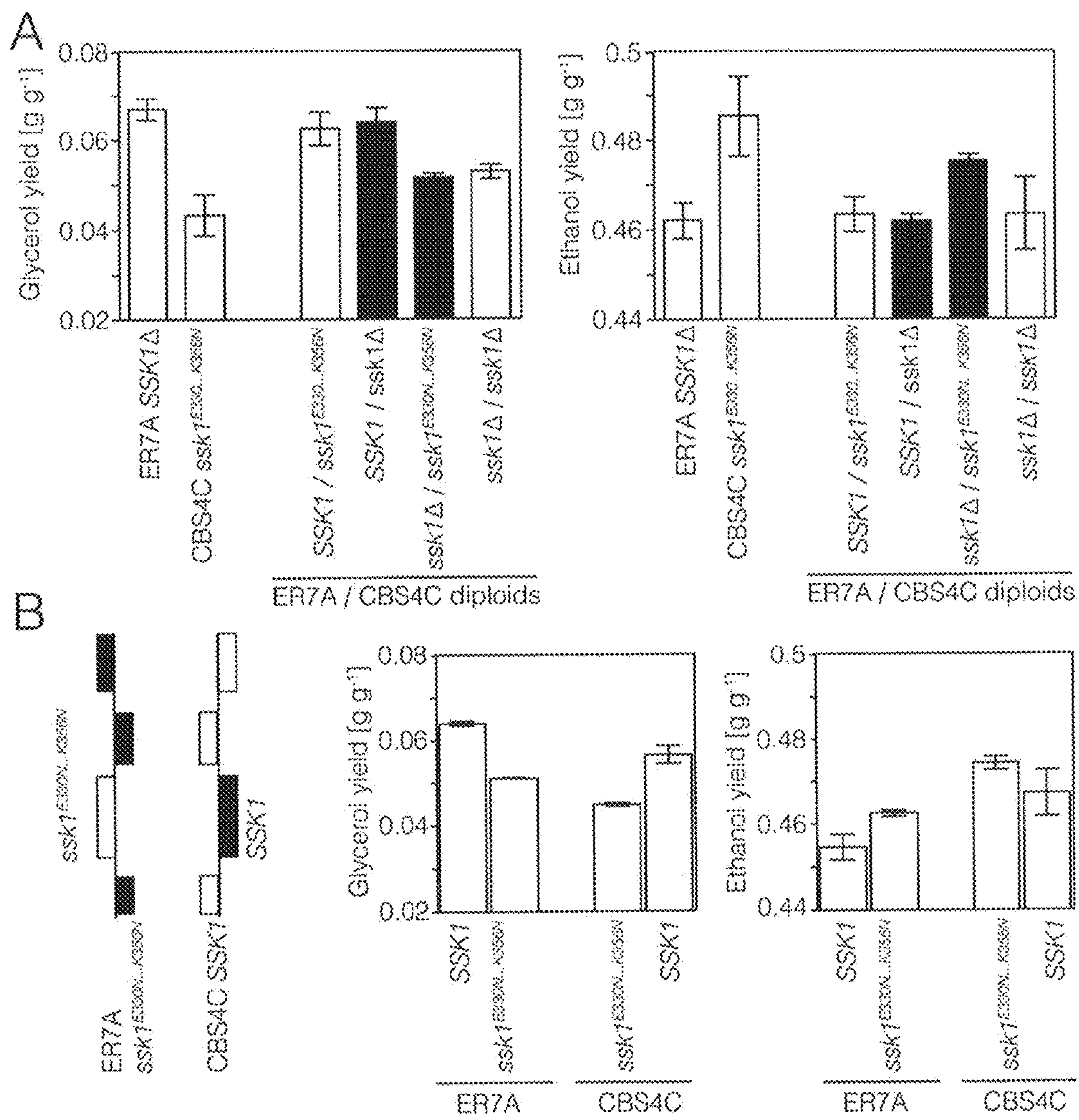
FIG. 6: Glycerol and ethanol yield after deletion or reciprocal exchange of the SSK1 alleles. (A) Comparison of the glycerol and ethanol yield of the two hemizygous strains with that of the ER7A and CBS4C parental strains and the SSK1/ssk1$^{E330N \ldots K356N}$ and ssk1Δ/ssk1Δ diploids. (B) Glycerol and ethanol yield in the ER7A and CBS4C parental strains without and with reciprocal exchange of the SSK1 and ssk1$^{E330N \ldots K356N}$ alleles.

The 20,000 bp region with the strongest linkage in the QTL on chromosome XII contained 13 genes, of which four genes contained non-synonymous mutations in the ORF (FIG. 4B). One of those four genes, SSK1, was located in the center of the QTL, which had a slightly stronger linkage. Ssk1 has a known function in the HOG pathway. Sequence comparison of the SSK1 alleles of the parental strains CBS4C and ER7A with the allele of the reference strain S288c revealed ten polymorphisms between the sequence of the SSK1 ORF in CBS4C and ER7A. A single base pair deletion at position 162,907 bp of Chr. XII was the most prominent mutation in the CBS4C SSK1 ORF, since it caused a reading frame shift and a new stop codon at position 357 in the protein. This resulted in a new primary amino acid sequence from position 330 until 356, while the wild-type Ssk 1 protein had a total length of 712 amino acids. Hence, we named the new allele ssk1$^{E330N \ldots K356N}$. The dramatic change in amino acid sequence and the truncation would normally be expected to result in a completely inactive protein and, therefore, in a phenotype similar to that of the ssk1Δ strain. However, this was not the case. The ssk1$^{E330N \ldots K356N}$ allele caused a different phenotype compared to deletion of SSK1 (see below). Next, we evaluated SSK1 as possible causative gene using reciprocal hemizygosity analysis (RHA) (Steinmetz et al., 2002). For that purpose, two CBS4C/ER7A hybrid and hemizygous diploid strains were constructed differing only in a single SSK1 allele, the other allele being deleted. The diploid strain with the single ssk1$^{E330N \ldots K356N}$allele derived from CBS4C showed a significantly reduced glycerol yield and a significantly higher ethanol yield than the diploid strain with the SSK1 allele from the ER7A strain (FIG. 5). This showed that ssk1$^{E330N \ldots K356N}$ was a causative gene in the QTL on chromosome XII. To evaluate whether the ssk1$^{E330N \ldots K356N}$ $^{a}$llele of CBS4C behaved as a recessive allele and whether it caused the same phenotype as deletion of SSK1, we also constructed a CBS4C/ER7A hybrid diploid strain with both SSK1 alleles deleted and compared its phenotype with that of CBS4C/ER7A with its original SSK1 alleles. The glycerol and ethanol yields of these strains were similar to that of the hemizygous diploid strain with the SSK1 allele from ER7A or the ssk1$^{E330N \ldots K356N}$ allele from CBS4C, respectively, (FIG. 6A). This indicates that the ssk1$^{E330N \ldots K356N}$ allele from CBS4C is a recessive allele and that ssk1$^{E330N \ldots K356N}$ behaves as a loss of function allele, at least in the hybrid background and the fermentation conditions used (100 ml anaerobic fermentations in minimal medium containing 5% glucose). When the glycerol yield (0.043 g. g-1) of the CBS4C parent strain was normalized to 100%, the glycerol yield of ER7A (147%) and that of the diploids ER7ACBS4C (145%) and ER7A/CBS4C ssk1Δ (148%) was very similar (FIG. 6A). In contrast, the strains ER7A ssk1Δ/CBS4C ssk1$^{E330N \ldots K356N}$ and ER7A ssk1Δ/CBS4C ssk1Δ had a glycerol yield of 119% and 122%, respectively, (FIG. 6A) suggesting that ssk1E330N . . . K356N was responsible for the majority of the reduction in glycerol yield in CBS4C compared to ER7A. This agrees with the result of the pooled-segregant whole-genome mapping, which revealed the SSK1 locus as the only QTL with significant linkage. To confirm the importance of SSK1 in an alternative way, we reciprocally exchanged the SSK1 alleles of CBS4C and ER7A by homologous recombination. Introduction of ssk1$^{E330N \ldots K356N}$ in the ER7A strain reduced its glycerol yield and enhanced its ethanol yield, while introduction of SSK1 in CBS4C enhanced its glycerol yield and reduced its ethanol yield (FIG. 6B). These results confirmed SSK1 as a causative allele for reduced glycerol and enhanced ethanol production in CBS4C. Given the recessive character of the ssk1$^{E330N \ldots K356N}$ allele, we tested its presence in the original diploid strain CBS6412 and found it to be present in two copies. This suggests that the unusual allele may provide a selective advantage in specific environmental niches.

Example 4

Figure 7:
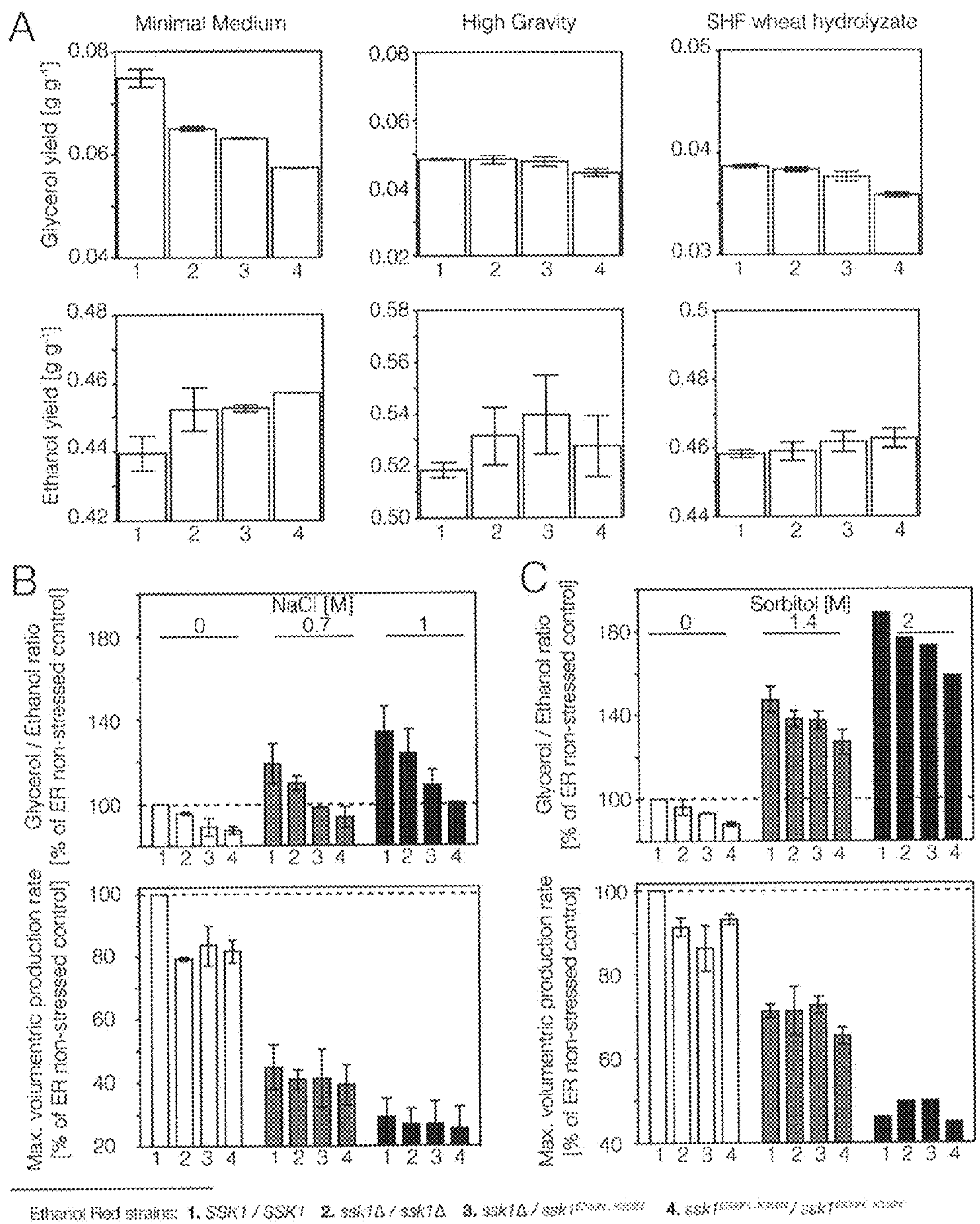
FIGS. 7A-7C: Glycerol and ethanol yields and osmostress tolerance in fermentations with the industrial bioethanol production strain Ethanol Red in which one or two copies of the ssk1$^{E330N \ldots K356N}$ allele had been introduced.

Reduction of the Glycerol/Ethanol Ratio in an Industrial Bioethanol Strain Using ssk1$^{E330N \ldots K356N}$ as a Novel Gene Tool To test the functionality of ssk1$^{E330N \ldots K356N}$ as a novel gene tool for reduction of glycerol yield under industrially relevant conditions, both SSK1 alleles of the industrial bioethanol production strain, Ethanol Red, were replaced by the ssk1$^{E330N \ldots K356N}$ variant using homologous recombination. In addition, an Ethanol Red ssk1Δ/ssk1Δ strain and an Ethanol Red ssk1$^{E330N \ldots K356N}$/ssk1Δ strain were constructed. These strains were tested in fermentations with minimal medium (5% wv glucose), high gravity medium (YP with 33% wv glucose) and wheat hydrolysate (SHF: Separate Hydrolysis and Fermentation). The results are shown in FIG. 7A. The double deletion of SSK1 reduced the glycerol yield. Interestingly, further reduction of glycerol yield was observed after introduction of one copy of ssk1$^{E330N \ldots K356N}$ while introduction of the second copy of ssk1$^{E330N \ldots K356N}$ lowered glycerol yield even more. Ethanol yields clearly increased in all Ethanol Red mutants compared to the wild-type strain in the minimal medium. The reduction of glycerol yield under high gravity or SHF conditions was generally less pronounced compared to minimal medium. Thus, the concomitant increase in ethanol yield in the Ethanol Red mutants was less obvious. Nevertheless, particularly the result obtained in minimal medium indicated that in the Ethanol Red diploid background the ssk1$^{E330N \ldots K356N}$ allele did not simply behave as a loss-of-function allele but had a stronger reducing effect on the glycerol/ethanol ratio than deletion of the SSK1 gene. These results confirm the usefulness of the ssk1$^{E330N \ldots K356N}$ allele as a novel gene tool for lowering glycerol production in industrial yeast strains.

Example 5

The Novel Gene Tool ssk1$^{E330N \ldots K356N}$ Retains Its Positive Effect Under High Osmolarity Conditions Several previous studies successfully reduced glycerol yield in *S. cerevisiae* with a concomitant increase in ethanol yield. However, many of the resulting strains showed a significantly reduced maximal volumetric ethanol production rate and increased sensitivity against osmotic stress (Bjorkqvist et al., 1997; Guadalupe Medina et al., 2010; Hubmann et al., 2011; Nissen et al., 2000a). In order to address this issue, we determined both the glycerol/ethanol ratio and the maximal volumetric ethanol production rate in the Ethanol Red strains containing one or two ssk1$^{E330N \ldots K356N}$ alleles under conditions of high osmolarity. In general, the cells produced higher levels of glycerol under hyperosmotic stress, i.e., in the presence of 1.4 M and 2 M sorbitol or 0.7 M and 1 M NaCl (FIGS. 7B and 7C). In spite of this, a similar improvement in the glycerol/ethanol ratio was observed in the Ethanol Red strains containing one or two ssk1$^{E330N \ldots K356N}$ alleles. The maximal volumetric ethanol production rate dropped with increasing osmolarity but this drop was not correlated with the presence or the number of ssk1$^{E330N \ldots K356N}$ alleles. Hence, the ssk1$^{E330N \ldots K356N}$ allele does not appear to cause an increase in osmosensitivity and retains its positive effect under conditions of high osmolarity. Close examination of the effect of ssk1$^{E330N \ldots K356N}$ on glycerol production in the Ethanol Red background also allows to make a quantitative assessment of the contribution of this allele to the phenotype. The initial glycerol yield was 167% of the CBS4C yield while the double insertion of ssk1$^{E330N \ldots K356N}$ caused a drop to 128% of the CBS4C yield. Hence, the ssk1 mutation appears to determine 50-60% of the trait. This indicates that the ssk1 mutation may be combined by other mutant alleles from other genes to obtain a maximal effect.

Example 6

Figure 8:
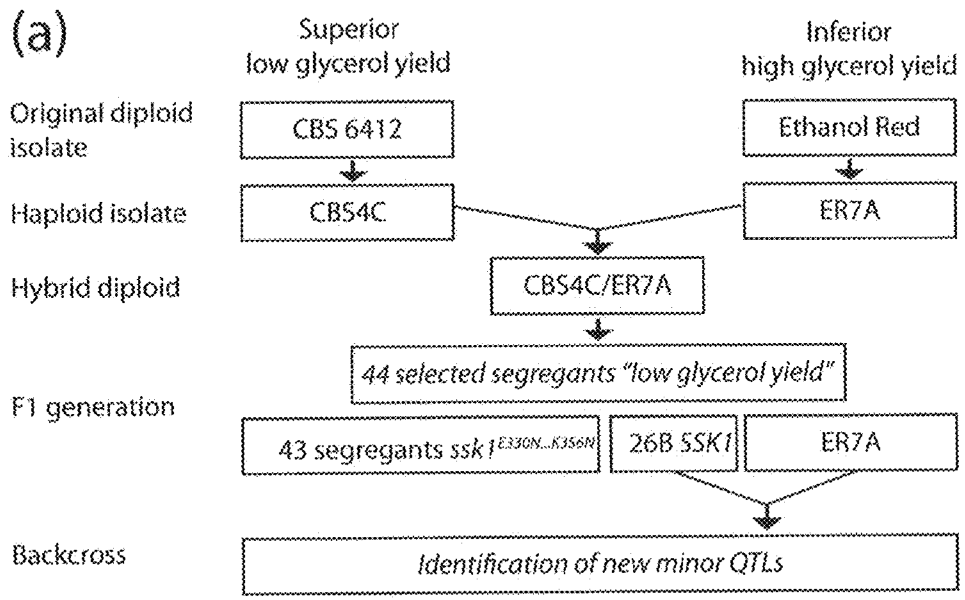
FIG. 8: Phenotypes of the parental strains ER7A and CBS4C and the segregant 26B. (a) Scheme of the crossings to map mutations linked to the low glycerol yield phenotype. The initial parental cross of ER7A and CBS4C resulted in the segregant 26B with a low glycerol phenotype but without the ssk1$^{E330N \ldots K356N}$ allele. The 26B segregant was crossed back with the inferior parent ER7A to find other linked mutations. (b) Glycerol and ethanol yield obtained in minimal medium with 5% glucose and in YP 10% glucose for the parental strains, ER7A and CBS4C, the segregant 26B, and the hybrid diploid 26B/ER7A.
Figure 8:
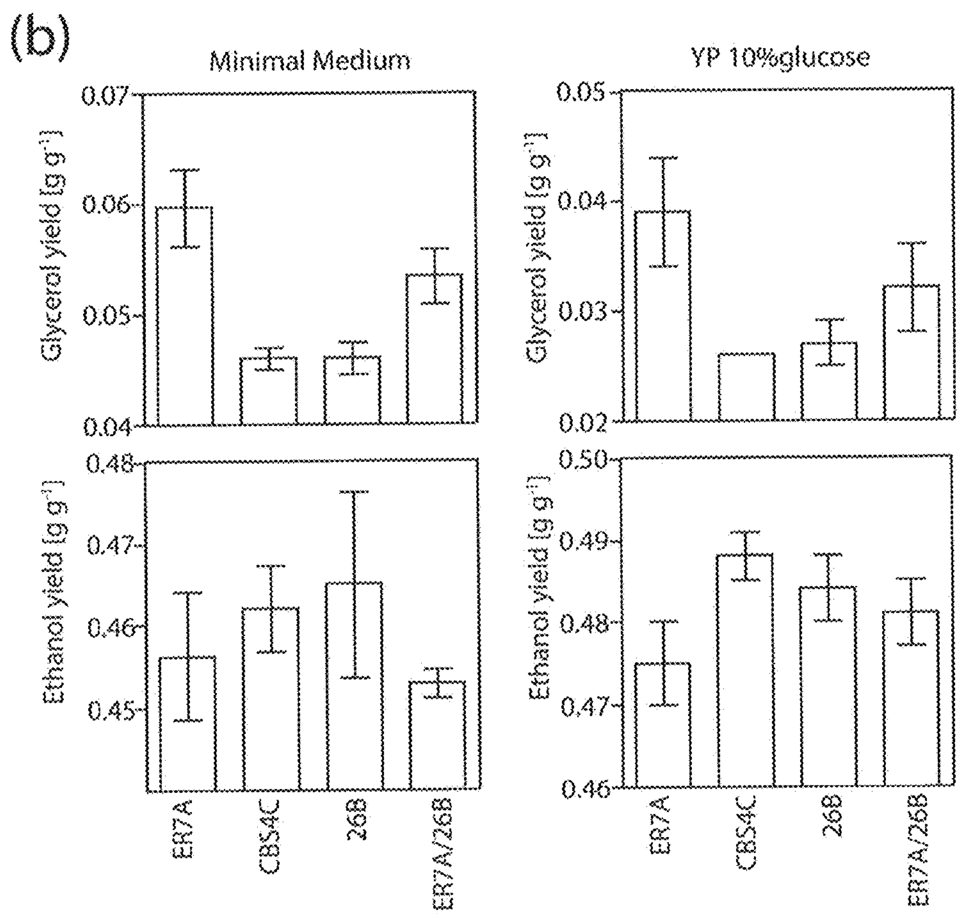

Selection of a Rare Segregant Displaying the Trait of Low Glycerol/High Ethanol Production and Lacking the ssk1$^{E330N \ldots K356N}$ Allele Previous work has identified the *S. cerevisiae* strain CBS6412 as a strain with an unusually low ratio of glycerol/ethanol production and genetic analysis identified the ssk1$^{E330N \ldots K356N}$ allele as a major causative gene (Hubmann et al., 2013) (FIG. 8*a*). In order to identify the minor QTLs and their causative genes responsible for determining this complex trait, we have first screened all superior segregants with a glycerol/ethanol ratio as low as the superior parent strain, for a segregant that lacked the ssk1$^{E330N \ldots K356N}$ allele. Among the 44 superior segregants available, only a single such segregant, 26B, was present. Its glycerol yield was equally low and its ethanol yield equally high as the superior parent strain CBS4C, both in minimal medium with 5% glucose and in rich yeast extract-peptone medium with 10% glucose (FIG. 8*b*). Hence, 26B showed the same phenotypic difference with the inferior parent strain ER7A as CBS4C (FIG. 8*b*).

Example 7

Backcross of the Unique Superior Segregant 26B with the Inferior Parent ER7A and Screening for Superior Segregants We subsequently switched the mating type of 26B from Matα to Mata (see materials and methods) and crossed the 26B strain with the inferior parent strain, ER7A, which is a derivative of the industrial strain Ethanol Red, currently used worldwide in bioethanol production. The hybrid diploid ER7A/26B showed an intermediate phenotype between ER7A and 26B (FIG. 8*b*). From this cross, 260 meiotic segregants were screened for low glycerol yield (and corresponding higher ethanol production) in 100 ml fermentations with YP 10% glucose. The parent strains 26B and ER7A, and the hybrid diploid, were used as controls in each batch of fermentations.

Figure 9:
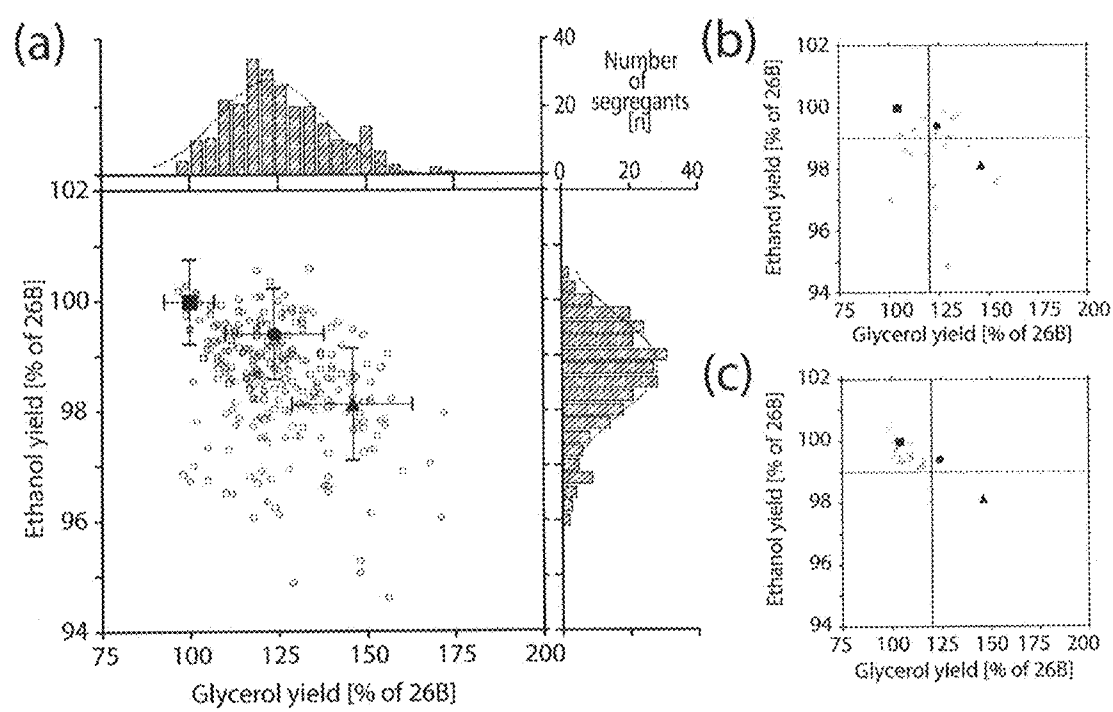
FIG. 9: Glycerol and ethanol yield in parental strains, hybrid diploid and segregants. (a) Glycerol and ethanol yield in the parental strains, 26B (■) and ER7A (▲), the hybrid diploid strain 26B/ER7A (●) and in segregants of 26B/ER7A (□). Fermentations were carried out in 100 ml YP with 10% glucose. Glycerol and Ethanol yields of all segregants, ER7A and the diploid 26B/ER7A were related to the yield of 26B, which was set as 100%. (b,c) Distribution of the glycerol and ethanol yield in the unselected (b) and selected (c) segregant pool of 26B/ER7A. The criteria for selection of "low glycerol" segregants (<120% glycerol yield, >99% ethanol yield) are indicated with stippled lines. The 22 selected segregants were fermented twice to confirm low glycerol production. These segregants were used for pooled-segregant whole-genome sequence analysis. The glycerol and ethanol yield of the parental strains, 26B and ER7A, and diploid 26B/ER7A are indicated as in (a).

Glycerol and ethanol yield of the segregants in each batch were normalized to those of 26B, which were set to 100%. ER7A and the diploid 26B/ER7A showed an average glycerol yield of 146% and 124% and a concomitantly decreased ethanol yield of 98.1% and 99.4% (FIG. 9*a*). The glycerol and ethanol yield showed a Gaussian distribution in the segregants, which extended over the range of the two parental stains. In the case of low glycerol yield, this extension was only marginal. The population mean of the glycerol yield (123%) and ethanol yield (98.8%) were located closely to that of the diploid 26B/ER7A. In general, glycerol and ethanol yield of the segregant population correlated inversely (as determined with a Pearson test), meaning that low glycerol yield usually resulted in high ethanol yield. Nearly all exceptions to this correlation were strains with an unusually low ethanol yield that failed to show a correspondingly higher glycerol yield. Two cut-off criteria were defined, a glycerol yield lower than 120% of 26B and an ethanol yield higher than 99% of 26B, which resulted in the selection of a set of 34 superior segregants. These were all retested in 100 ml fermentations with YP 10% glucose and 22 segregants showed again a low glycerol yield combined with a correspondingly higher ethanol yield (FIG. 9*b*). These 22 segregants were selected for QTL mapping with pooled-segregant whole-genome sequence analysis. A second pool with 22 randomly selected segregants was also subjected to pooled-segregant whole-genome sequence analysis and used as the unselected control pool (FIG. 9*b*).

Example 8

Pooled-Segregant Whole-Genome Sequence Analysis and QTL Mapping

Figure 10:
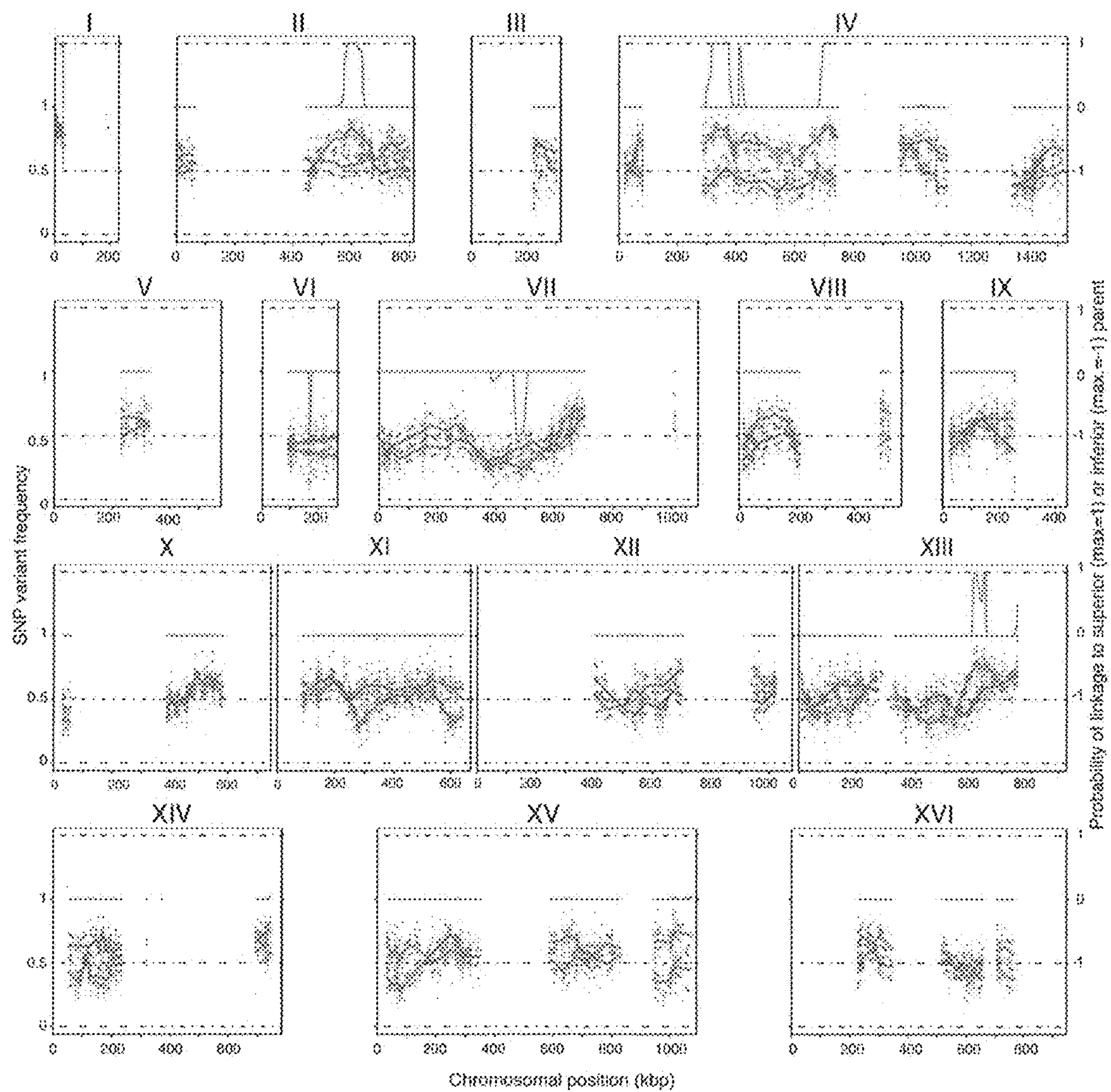
FIG. 10: Plots of SNP variant frequency versus chromosomal position and corresponding probability of linkage to the superior or inferior parent. Plots of SNP variant frequency versus chromosomal position in all 16 yeast chromosomes for the selected (raw data: light grey triangles; smoothed data: red line) and unselected pool (raw data: light grey circles; smoothed data: green line). Significant upward deviations from the average of 0.5 indicate linkage to the superior parent 26B, while significant downward deviations indicate linkage to the inferior parent ER7A. The smoothed line was determined as described previously (Swinnen et al., 2012; Claesen et al., 2013). Linked regions were detected with EXPLoRA.

The genomic DNA of the selected and unselected pools, as well as the parent strain 26B, was extracted and submitted to custom sequence analysis using Illumina HiSeq 2000 technology (BGI, Hong Kong, China). The parent strain ER7A has been sequenced in our previous study (data accession number SRA054394) (Hubmann et al., 2013). Read mapping and SNP filtering were carried out as described previously (Swinnen et al., 2012; Claesen et al., 2013). The SNP variant frequency was plotted against the SNP chromosomal position (FIG. 10). Of the total number of 21,818 SNPs between CBS4C and ER7A, 5,596 SNPs of CBS4C were found back in 26B. These SNPs were used for mapping minor QTLs in the genomic areas that were not identical between 26B and ER7A. The other genomic areas were completely devoid of SNPs because they were identical between the 26B and ER7A parents (FIG. 10). The scattered raw SNP variant frequencies were smoothened and a confidence interval was calculated, as previously described (Swinnen et al., 2012; Claesen et al., 2013). The Hidden Markow Model, EXPloRA (see Materials and Methods) was used to evaluate whether candidate regions showed significant linkage to the low glycerol phenotype. EXPloRA reported six candidate QTLs: on chr. I (3859-11045), chr. II (584232-619637), chr. IV (316389-375978 and 696486-748140), and chr. XIII (600902-610995 and 634582-640415) for the selected segregants pool.

The locus on chr. I was present in both the selected and unselected pool and was thus likely linked to an inadvertently selected trait, such as sporulation capacity or spore viability. It was excluded from further analysis. The locus on chr. II was also present in the previous mapping with the two original parents, CBS4C and ER7A, but in that case it was not pronounced enough to be significant (Hubmann et al., 2013). The backcross has now confirmed its relevance. On chr. IV and XIII, new QTLs were detected, which were not present in the mapping with the original parent strains CBS4C and ER7A.

EXPloRA also reported two significantly linked loci on chr. VI (169586-170209) and chr. VII (472620-493523) for the unselected pool. Both loci were linked to the inferior parent, ER7A. For the region on chr. VII, the linked locus with the inferior parent genome was also present in the selected pool. Both loci likely represent linkage to inadvertently selected traits, such as sporulation capacity or spore viability. It is unclear why the locus on chr. VI was only present in the unselected pool. Since both loci were not linked to the low glycerol phenotype they were not investigated further.

Figure 11:
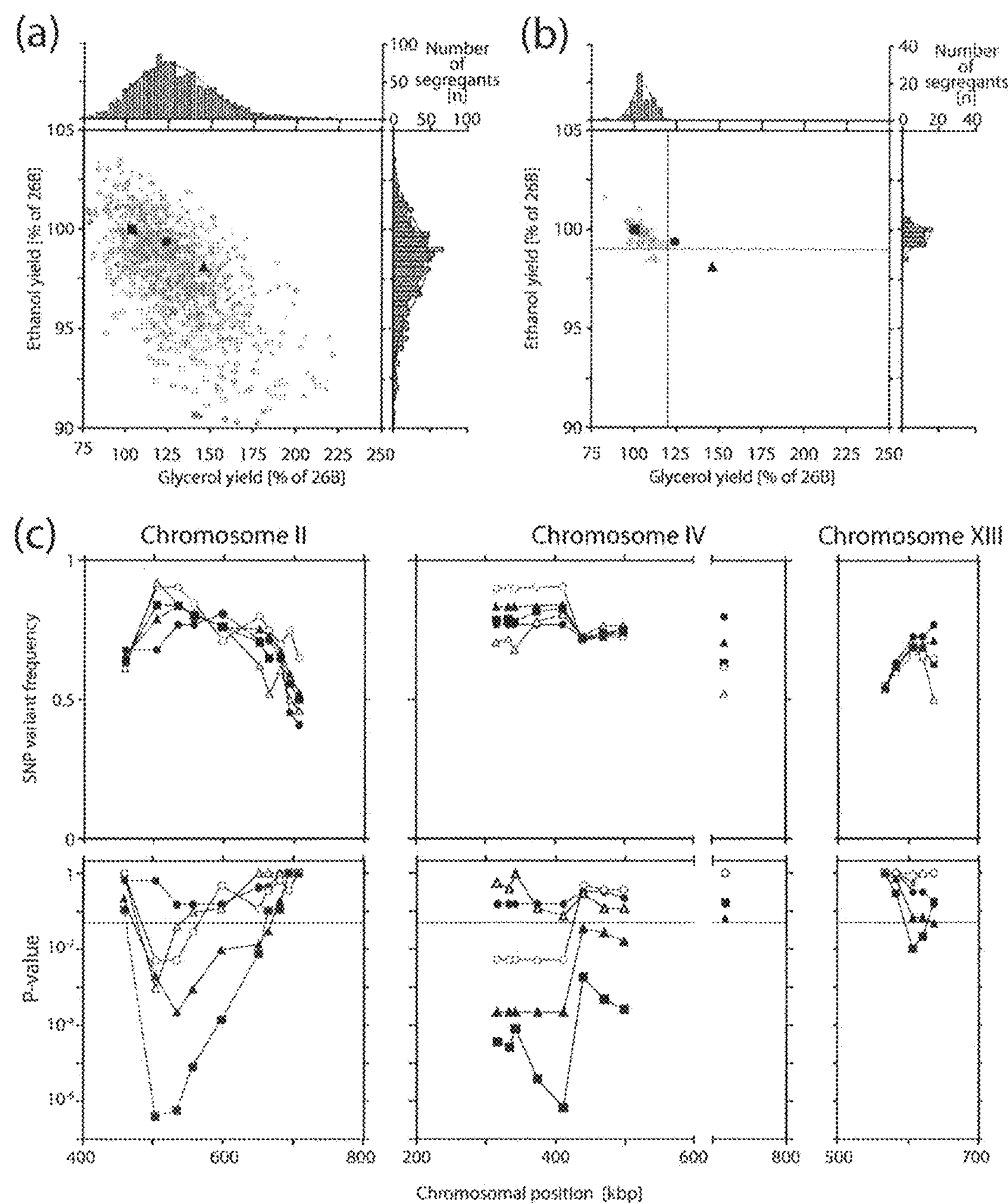
FIG. 11: Linkage analysis of QTLs on chr. II, IV and XIII with different groups of segregants. (a) Glycerol and ethanol yield of the parental strains, 26B (■) and ER7A (▲), and the hybrid diploid strain 26B/ER7A (●). Glycerol and ethanol yield of the first isolated F1 segregants from 26B/ER7A (○), of the additional F1 segregants (□) and of the F5 segregants (◇). Fermentations were carried out in 5 ml YP 10% glucose. Glycerol and ethanol yield of all segregants, ER7A and the diploid 26B/ER7A were related to the yield of 26B, which was set as 100%. (b) Segregants were selected for low glycerol (<120% glycerol yield, stippled line) and high ethanol (>99% ethanol yield, stippled line) after each round of screening, resulting in the following segregant groups: 22 F1 segregants used for pooled-segregant whole-genome sequence analysis (○), 22 additional selected F1 segregants (○), and 26 F5 segregants (◇). These segregants were reconfirmed in 100 ml YP 10% glucose. (c) SNP variant frequency (top) and respective P-value (bottom) were determined by allele-specific PCR in individual segregants of the sequenced selected pool (●), additional F1 selected pool (○), the total F1 selection of 44 (▲), the selection of F5 segregants (Δ), and the total selection of all 70 segregants (■) to fine-map the QTLs on chr. II, IV and XIII, which were detected with EXPloRA. The statistical confidence line (for P-value≤0.05) is indicated with a stippled line.

The QTLs on chr. II, IV and XIII were further investigated in detail. Selected individual SNPs were scored in the 22 individual superior segregants to determine precisely the SNP variant frequency and the statistical significance of the putative linkage. However, using the binomial test previously described (Swinnen et al., 2012; Claesen et al., 2013) none of the three loci was found to be significantly linked to the genome of the superior parent strain 26B with the number of segregants available. Therefore, we screened 400 additional F1 segregants of the diploid 26B/ER7A for low glycerol/high ethanol production. In addition, we performed four rounds of random inbreeding with a very large number of F1 segregants from the diploid 26B/ER7A to increase the recombination frequency (Parts et al., 2011) and subsequently evaluated 400 F5 segregants in small-scale fermentations for glycerol/ethanol yield. The results for the 400 F1 and 400 F5 segregants are shown in FIG. 11*a*. The glycerol and ethanol yields are expressed as percentage of that of the superior parent strain 26B. There was again a clear inverse relationship between glycerol and ethanol yield. From the 800 segregants, we selected in total 48 superior segregants, 22 F1 segregants and 26 F5 segregants (FIG. 11*b*).

We next scored selected SNPs in the putative QTLs on chr. II, IV and XIII in all individual segregants, i.e., the 22 segregants of the sequenced selected pool, the 22 additional selected F1 segregants, the total of 44 selected F1 segregants, the 26 selected F5 segregants and the total of 70 selected segregants. The mean SNP variant frequency for these groups of segregants and the corresponding P-value were calculated as described previously (Swinnen et al., 2012; Claesen et al., 2013) and are shown in FIG. 11*c*. For the three QTLs we could now demonstrate significant linkage (P-value<0.05) to the genome of the superior parent strain 26B. For the QTLs on chr. II and IV the linkage was now very strong, while for the QTL on chr. XIII it was still weak, but significant. On the other hand, the second region on chr. IV did not show significant linkage with none of the pools.

Example 9

Identification of Causative Genes in the QTLs on chr. II, IV and XIII

We selected three candidate genes in the three QTLs based on their known function in glycerol metabolism. SMP1, which is located in the QTL on chr. II (594,864 to 593,506 bp), encodes a putative transcription factor involved in regulating glycerol production during the response to osmostress (de Nadal et al., 2003). The gene is located in the chromosomal region from 584,232 to 619,637 bp, which was predicted as most significant by the EXPloRA model. The 26B SMP1 allele has two point mutations, which are changing the primary protein sequence at position 110 from arginine to glycine and at position 269 from proline to glycine. Hence, we have named this allele smp1$^{R110Q,P269Q}$.

On chr. IV, the SNP with the highest linkage was located at position 411,831 bp (FIG. 11*c*), which is within the open reading frame of GPD1 (411,825 to 413,000 bp). This is the structural gene for the NAD+-dependent cytosolic glycerol 3-phosphate dehydrogenase (Larsson et al., 1993; Albertyn et al., 1994). It catalyzes the conversion of dihydroxyacetone phosphate (DHAP) to glycerol 3-phosphate through the oxidation of NADH. The GPD1 allele of 26B harbors a point mutation, changing leucine at position 164 into proline. This mutation was found earlier (DDBJ database data, accession number AY598965). The GPD1 allele of 26B was named gpd1$^{L164P}$.

On chr. XIII, the SNP with the highest linkage was located at position 606,166 by (FIG. 11*c*), which is within the open reading frame of HOT1 (605,981 to 608,140 bp). HOT1 encodes a transcription factor required for the response to osmotic stress of glycerol biosynthetic genes, including GPD1, and other HOG-pathway regulated genes (Alepuz et al., 2003; Rep et al., 1999). The 26B HOT1 allele contains two non-synonymous point mutations, changing proline at position 107 to serine and histidine at position 274 to tyrosine. We have named the HOT1 allele of 26B, $hot1^{P107S,H274Y}$.

Figure 12:
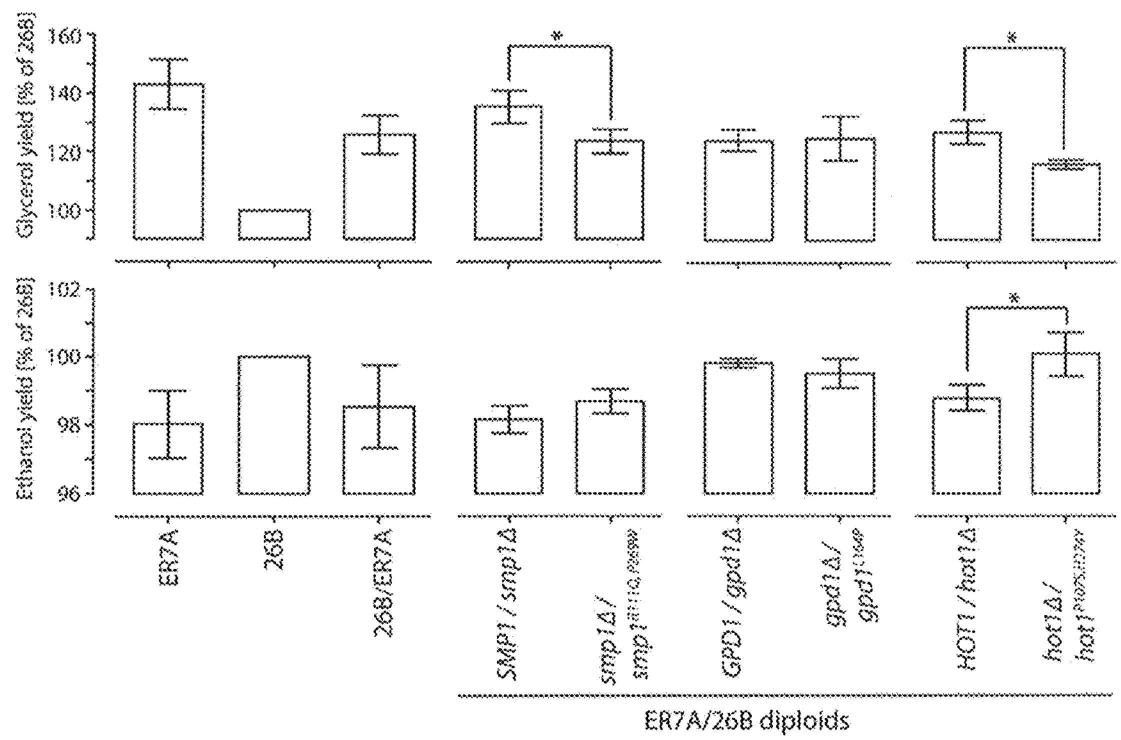
FIG. 12: Reciprocal hemizygosity analysis (RHA). RHA for the candidate genes, SMP1 (chr. II), GPD1 (chr. IV), and HOT1 (chr. XIII) to evaluate them as causative genes in the QTLs. For RHA, diploid strains were constructed with either the deletion of the ER7A allele or the deletion of the 26B allele. Glycerol and ethanol yield of the two hemizygous diploid strains were related to the parental strain 26B. The Student t-test was used to confirm significant differences in glycerol and ethanol yield for the two diploids and is indicated with *.

We first investigated the effect of $smp1^{R110Q,P269Q}$, $gpd1^{L164P}$ and $hot1^{P107S,H274Y}$ on the low glycerol/high ethanol phenotype using reciprocal hemizygosity analysis (RHA) (Steinmetz et al., 2002). For that purpose, we constructed for each gene a pair of hemizygous diploid 26B/ER7A hybrid strains, in which each pair contained a single copy of the superior allele or the inferior allele of SMP1, GPD1 or HOT1, respectively. The three pairs of hemizygous diploids were tested in the same 100 ml YP 10% glucose fermentations as used for the screening. The parent strains 26B and ER7A and the hybrid diploid 26B/ER7A were added as controls. The glycerol and ethanol yields were expressed as percentage of those of 26B, which were set at 100%. The significance of any differences between the strains was evaluated using a two-tailed unpaired t-test with a $P\text{-value}<0.05$ considered to indicate a significant difference. The results of the RHA are shown in FIG. 12. They indicate that both $smp1^{R110Q,P269Q}$ and $hot1^{P107S,H274Y}$ but not $gpd1^{L164P}$, derived from the superior parent 26B cause a significant drop in the glycerol/ethanol ratio compared to the alleles of the inferior parent strain ER7A. For $smp1^{R110Q,P269Q}$ only the reduction in glycerol, and not the increase in ethanol, was significant with the $P\text{-value}<0.05$ used. These results indicate that $smp1^{R110Q,P269Q}$ is a causative gene in the QTL on chr. II. They do not exclude that the QTL may still contain a second causative gene, especially since $smp1^{R110Q,P269Q}$ is not located in the region with the strongest linkage (lowest P-value).

The RHA with the GPD1 alleles failed to show any difference both for glycerol and ethanol production (FIG. 12). Hence, the superior character of the $gpd1^{L164P}$ allele could not be confirmed with RHA. This is remarkable because the SNP with the strongest linkage (lowest P-value) in the QTL on chr. IV was located in the open reading frame of GPD1 and showed very strong linkage to the low glycerol/high ethanol phenotype. The $hot1^{P107S,H274Y}$ allele of the superior strain 26B, on the other hand, caused a reduction in glycerol and an increase in ethanol production, and both changes were significant ($P\text{-value}<0.05$) (FIG. 12). Hence, these results indicate that $hot1^{P107S,H274Y}$ is a causative allele in the QTL on chr. XIII and because it contains the SNP with the strongest linkage (lowest P-value), it is likely the main causative allele in this QTL.

The glycerol yield for the inferior parent ER7A and the diploid 26B/ER7A were on average 143% and 126% of the 26B yield (FIG. 12). Ethanol yield of both strains was correspondingly reduced to 98% and 98% of the 26B yield, respectively. Clearly, the $smp1^{R110Q,P269Q}$ and $hot1^{P107S,H274Y}$ alleles can only be responsible for part of the difference in the glycerol/ethanol ratio between the parent strains. The same was found previously for the $ssk1^{E330N \ldots K356N}$ allele (Hubmann et al., 2013). This confirms that the glycerol/ethanol ratio in yeast fermentation is a true polygenic, complex trait, determined by an interplay of multiple mutant genes.

Example 10

Figure 13:
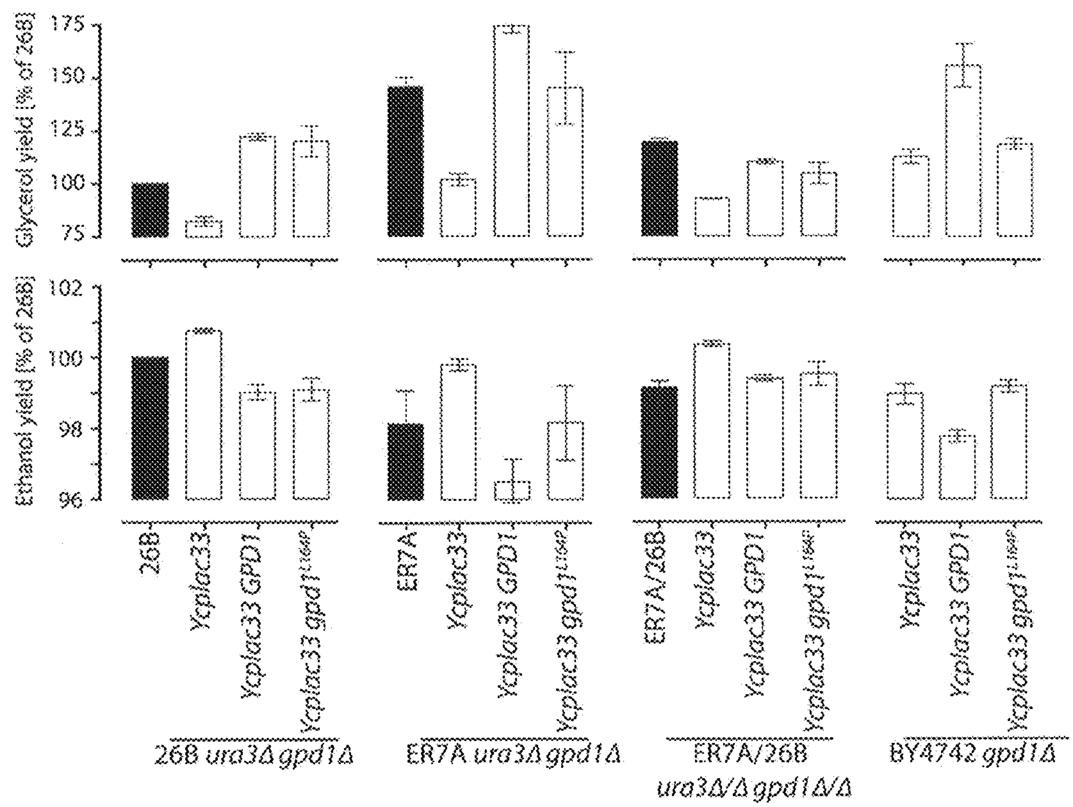
FIG. 13: Expression of gpd1$^{L164P}$-CBS4C and GPD1-ER7A in segregant 26B, ER7A, the diploid 26B/ER7A and BY4742. Glycerol and ethanol yield in the gpd1Δ strains, 26B, ER7A, 26B/ER7A and BY4742, harboring the plasmids YCplac33, YCplac33 GPD1-ER7A, and YCplac33 gpd1$^{L164P}$-CBS4C. Fermentations were carried out in 100 ml YP 10% glucose. Glycerol and ethanol yield of the strains were related to the yield of 26B, which was set at 100%. In the BY 4742 and ER7A backgrounds, which lack the smp1$^{R110Q,P269Q}$ and hot1$^{P107S,H274Y}$ alleles, the gpd1$^{L164P}$ allele clearly reduced glycerol yield and concomitantly increased ethanol yield compared to the wild-type GPD1 allele. In the strains 26B and 26B/ER7A, which contain the smp1$^{P110Q,P269Q}$ and hot1$^{P107S,H274Y}$ alleles, the gpd1L164P allele resulted in a similar glycerol yield as the wild-type GPD1 allele.

Expression of the $gpd1^{L164P}$ Allele from 26B in Haploid gpd1Δ Strains Reveals Its Superior Character Several explanations could account for the failure to confirm the superior character of the $gpd1^{L164P}$ allele from 26B in the RHA test. A closely located gene may be the real causative gene, the $gpd1^{L164P}$ allele may be effective only in a haploid genetic background or the effect of the $gpd1^{L164P}$ allele may be suppressed through epistasis by one or both of the other two superior alleles, $smp1^{R110Q,P269Q}$ and $hot1^{P107S,H274Y}$. To distinguish between these possibilities, we amplified the gpd1L164P allele from strain CBS4C and the GPD1 allele from strain ER7A by PCR (410,523 to 413,479 bp, including promotor, ORF and terminator). The PCR fragment was ligated in the centromeric plasmid YCplac33, resulting in plasmids YCplac33/$gpd1^{L164P}$-CBS4C and YCplac33/GPD1-ER7A. Both plasmids were transformed into gpd1Δ strains of the two parents 26B and ER7A, the hybrid diploid 26B/ER7A and the lab strain BY4742 (Giaever et al., 2002; Winzeler et al., 1999). All strains were tested in 100 ml scale fermentations with YP 10% glucose. Glycerol and ethanol yield were determined after 120 h fermentation and were expressed as percentage of those of 26B. The results are shown in FIG. 13.

The expression of the $gpd1^{L164P}$-CBS4C or GPD1-ER7A allele in the gpd1Δ strains of the superior parent 26B and the hybrid diploid 26B/ER7A enhanced glycerol production and reduced ethanol production to the same extent for the two alleles. On the other hand, in the gpd1Δ strains of the inferior parent ER7A and the lab strain BY4742, the $gpd1^{L164P}$-CBS4C allele enhanced glycerol production and reduced ethanol production significantly more than the GPD1-ER7A allele. The latter shows that the $gpd1^{L164P}$-CBS4C allele is superior compared to the GPD1-ER7A allele. The difference between the two alleles is apparently not dependent on the haploid or diploid background of the strain but seems to be related with the presence of the two other superior alleles, $smp1^{R110Q,P269Q}$ and $hot1^{P107S,H274Y}$. They are both present in the two strains, 26B and 26B/ER7A, in which $gpd1^{L164P}$-CBS4C has no differential effect and absent in the two strains, ER76A and BY4742, in which $gpd1^{L164P}$-CBS4C causes a differential effect. Hence, the superior potency of $gpd1^{1164P}$-CBS4C is likely suppressed through epistasis by $smp1^{R110Q,P269Q}$ and $hot1^{P107S,H274Y}$.

Figure 14:
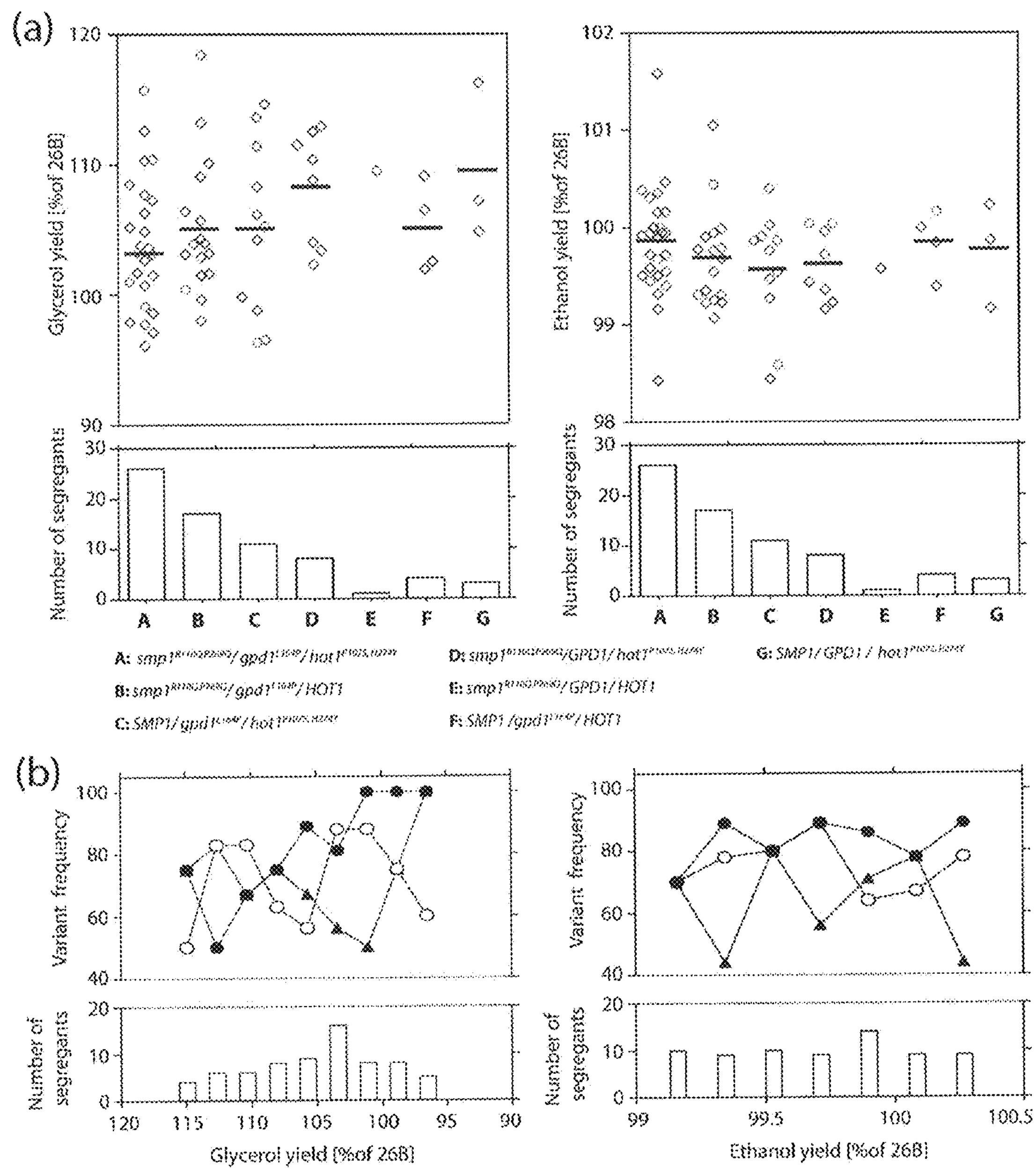
FIG. 14: Distribution of the gpd1$^{L164P}$, hot1$^{P107S,H274Y}$ and smp1$^{R110Q,P269Q}$ alleles in the selected low glycerol/high ethanol segregants. (a) Glycerol and ethanol yield in segregants with different combinations of the superior alleles, gpd1$^{L164P}$, hot1$^{P107S,H274Y}$ and smp1$^{R110Q,P269Q}$, in the selected segregant pool. The mean value of the glycerol and ethanol yield is indicated for each group. (b) Variant frequency of gpd1$^{L164P}$ (●), hot1$^{107S,H274Y}$ (▲) and smp1$^{R110Q,P269Q}$ (○) in the 70 selected segregants, which were categorized according to decreasing glycerol yield and increasing ethanol yield. Glycerol yield was divided into nine bins, each with a similar number of strains, starting from <96.5 and with a bin width of 2.3%. Accordingly, ethanol yield was divided into seven bins, each with a similar number of strains, starting from <99.16 and with a bin width of 0.185%. The number of segregants in each bin is indicated in the lower panel.

We have scored the final 70 superior segregants with a glycerol production <120% and an ethanol production >99% of that of the superior parent 26B, for the presence of the three causative alleles, $smp1^{R110Q,P269Q}$, $gpD1^{lL164P}$ and $hot1^{P107S,H274Y}$. The results are shown in FIG. 14*a*. The largest group of superior segregants contained all three mutant alleles, followed by smaller groups with only two of the three mutant alleles and finally the three smallest groups with only one mutant allele. Hence, there was a clear correlation between the number of the mutant alleles and low glycerol/high ethanol yield in this group of selected segregants. On the other hand, although there was a tendency for a lower mean glycerol/ethanol production ratio with an increasing number of mutant alleles, the differences between the means of the different groups were small. We have also investigated a possible correlation between the different mutant alleles and the strength of the low glycerol/high ethanol phenotype. For that purpose, we determined the percentage of segregants with a specific mutant allele in sets of strains with a different glycerol/ethanol ratio. The results show that there is no preference between the different alleles in the strains with a higher glycerol/ethanol ratio, but in the strains with the lowest glycerol/ethanol ratio the $gpd1^{L164P}$ allele is preferentially present, followed by the $hot1^{P107S,H274Y}$ allele, although the latter is only true in the category with the lowest glycerol/ethanol ratio (FIG. 14*b*). Hence, the order of potency of the three alleles appears to be: $gpd1^{L164P}>hot1^{P107S,H274Y}\geq smp1^{R110Q,P269Q}$. There was no correlation between the variant frequency of the three alleles for low glycerol yield and high ethanol yield, indicating that other minor QTLs may independently affect ethanol yield more than the three new alleles identified or that it is the combination of the alleles that is important.

REFERENCES

Akada R, Hirosawa I, Kawahata M, Hoshida H, Nishizawa Y (2002) Sets of integrating plasmids and gene disruption cassettes containing improved counterselection markers designed for repeated use in budding yeast. Yeast 19: 393-402.

Akada R, Matsuo K, Aritomi K, Nishizawa Y (1999) Construction of recombinant sake yeast containing a dominant FAS2 mutation without extraneous sequences by a two-step gene replacement protocol. J Biosci Bioeng 87: 43-48.

Albers E, Larsson C, Liden G, Niklasson C, Gustafsson L (1996) Influence of the nitrogen source on *Saccharomyces cerevisiae* anaerobic growth and product formation. Appl Environ Microbiol 62: 3187-3195.

Albertyn J, Hohmann S, Thevelein J M, Prior B A (1994) GPD1, which encodes glycerol-3-phosphate dehydrogenase, is essential for growth under osmotic stress in *Saccharomyces cerevisiae*, and its expression is regulated by the high-osmolarity glycerol response pathway. Mol Cell Biol 14: 4135-4144.

Alepuz P M, de Nadal E, Zapater M, Ammerer G, Posas F: Osmostress-induced transcription by Hot1 depends on a Hog1-mediated recruitment of the RNA Pol II. EMBO J 2003, 22:2433-2442.

Alfenore S, Cameleyre X, Benbadis L, Bideaux C, Uribelarrea J L, Goma G, Molina-Jouve C, Guillouet S E (2004) Aeration strategy: a need for very high ethanol performance in *Saccharomyces cerevisiae* fed-batch process. Appl Microbiol Biotechnol 63: 537-542.

Alper H, Moxley J, Nevoigt E, Fink G R, Stephanopoulos G (2006) Engineering yeast transcription machinery for improved ethanol tolerance and production. Science 314: 1565-1568.

Ansell R, Granath K, Hohmann S, Thevelein J M, Adler L (1997) The two isoenzymes for yeast NAD+-dependent glycerol 3-phosphate dehydrogenase encoded by GPD1 and GPD2 have distinct roles in osmoadaptation and redox regulation. Embo J 16:2179-2187.

Bai F W, Anderson W A, Moo-Young M (2008) Ethanol fermentation technologies from sugar and starch feedstocks. Biotechnol Adv 26: 89-105.

Bailey J E, Sburlati A, Hatzimanikatis V, Lee K, Renner W A, Tsai P S (1996) Inverse metabolic engineering: A strategy for directed genetic engineering of useful phenotypes. Biotechnol Bioeng 52: 109-121.

Bakker B M, Overkamp K M, van Maris A J, Kotter P, Luttik M A, van Dijken J P, Pronk J T (2001) Stoichiometry and compartmentation of NADH metabolism in *Saccharomyces cerevisiae*. FEMS Microbiol Rev 25: 15-37.

Basso L C, de Amorim H V, de Oliveira A J, Lopes M L (2008) Yeast selection for fuel ethanol production in Brazil. FEMS Yeast Res 8: 1155-116.

Bideaux C, Alfenore S, Cameleyre X, Molina-Jouve C, Uribelarrea J L, Guillouet S E (2006) Minimization of glycerol production during the high-performance fed-batch ethanolic fermentation process in *Saccharomyces cerevisiae*, using a metabolic model as a prediction tool. Appl Environ Microbiol 72: 2134-2140.

Bjorkqvist S, Ansell R, Adler L, Liden G (1997) Physiological response to anaerobicity of glycerol-3-phosphate dehydrogenase mutants of *Saccharomyces cerevisiae*. Appl Environ Microbiol 63: 128-132.

Blomberg A, Adler L (1989) Roles of glycerol and glycerol-3-phosphate dehydrogenase (NAD+) in acquired osmotolerance of *Saccharomyces cerevisiae*. J Bacteriol 171: 1087-1092.

Brem R B, Yvert G, Clinton R, Kruglyak L (2002) Genetic dissection of transcriptional regulation in budding yeast. Science 296: 752-755.

Brewster J, de Valoir T, Dwyer N, Winter E, Gustin M (1993) An osmosensing signal transduction pathway in yeast. Science 259: 1760-1763.

Bro C, Regenberg B, Forster J, Nielsen J (2006) In silico aided metabolic engineering of *Saccharomyces cerevisiae* for improved bioethanol production. Metab Eng 8: 102-111.

Cambon B, Monteil V, Remize F, Camarasa C, Dequin S (2006) Effects of GPD1 overexpression in *Saccharomyces cerevisiae* commercial wine yeast strains lacking ALD6 genes. Appl Environ Microbiol 72: 4688-4694.

Claesen J, Clement L, Shkedy Z, Foulquie-Moreno M R, Burzykowski T: Simultaneous mapping of multiple gene loci with pooled segregants. PLoS One 2013, In press.

de Nadal E, Casadome L, Posas F: Targeting the MEF2-like transcription factor Smp1 by the stress-activated Hog1 mitogen-activated protein kinase. Mol Cell Biol 2003, 23:229-237.

Deutschbauer A M, Davis R W (2005) Quantitative trait loci mapped to single nucleotide resolution in yeast. Nat Genet 37: 1333-1340.

Duitama J, Srivastava P K, Mandoiu II (2012) Towards accurate detection and genotyping of expressed variants from whole transcriptome sequencing data. BMC Genomics 13(Suppl 2): S6.

Eglinton J M, Heinrich A J, Pollnitz A P, Langridge P, Henschke P A, de Barros Lopes M (2002) Decreasing acetic acid accumulation by a glycerol overproducing strain of *Saccharomyces cerevisiae* by deleting the ALD6 aldehyde dehydrogenase gene. Yeast 19: 295-301.

Ehrenreich I M, Torabi N, Jia Y, Kent J, Martis S, Shapiro J A, Gresham D, Caudy A A, Kruglyak L (2010) Dissection of genetically complex traits with extremely large pools of yeast segregants. Nature 464: 1039-1042.

Ehsani M, Fernandez M R, Biosca J A, Julien A, Dequin S (2009) Engineering of 2,3-butanediol dehydrogenase to reduce acetoin formation by glycerol-overproducing, low-alcohol *Saccharomyces cerevisiae*. Appl Environ Microbiol 75: 3196-3205.

Gardner N, Rodrigue N, Champagne C P (1993) Combined effects of sulfites, temperature, and agitation time on production of glycerol in grape juice by *Saccharomyces cerevisiae*. Appl Environ Microbiol 59: 2022-2028.

Geertman J M, van Maris A J, van Dijken J P, Pronk J T (2006) Physiological and genetic engineering of cytosolic redox metabolism in *Saccharomyces cerevisiae* for improved glycerol production. Metab Eng 8: 532-542.

Giaever G, Chu A M, Ni L, Connelly C, Riles L, Veronneau S, Dow S, Lucau-Danila A, Anderson K, Andre B, et al.: Functional profiling of the *Saccharomyces cerevisiae* genome. Nature 2002, 418:387-391.

Gietz D, St Jean A, Woods R A, Schiestl R H (1992) Improved method for high efficiency transformation of intact yeast cells. Nucleic Acids Res 20: 1425.

Guadalupe Medina V, Almering M J, van Maris A J, Pronk J T (2010) Elimination of glycerol production in anaerobic cultures of a *Saccharomyces cerevisiae* strain engineered to use acetic acid as an electron acceptor. Appl Environ Microbiol 76: 190-195.

Gueldener U, Heinisch J, Koehler G J, Voss D, Hegemann J H (2002) A second set of loxP marker cassettes for Cre-mediated multiple gene knockouts in budding yeast. Nucleic Acids Res 30: e23.

Heux S, Sablayrolles J M, Cachon R, Dequin S (2006) Engineering a *Saccharomyces cerevisiae* wine yeast that exhibits reduced ethanol production during fermentation under controlled microoxygenation conditions. Appl Environ Microbiol 72: 5822-5828.

Hoffman C S, Winston F (1987) A ten-minute DNA preparation from yeast efficiently releases autonomous plasmids for transformation of *Escherichia coli*. Gene 57: 267-272.

Hohmann S (2002) Osmotic stress signaling and osmoadaptation in yeasts. Microbiol Mol Biol Rev 66: 300-372.

Homer N, Merriman B, Nelson S F (2009) BFAST: an alignment tool for large scale genome resequencing. PLoS One 4: e7767.

Hubmann G, Guillouet S, Nevoigt E (2011) Gpd1 and Gpd2 fine-tuning for sustainable reduction of glycerol formation in *Saccharomyces cerevisiae*. Appl Environ Microbiol 77: 5857-5867.

Hubmann G, Foulquie-Moreno M R, Nevoigt E, Duitama J, Meurens N, Pais T M, Mathe L, Saerens S, Nguyen H T T, Swinnen S, et al.: Quantitative trait analysis of yeast biodiversity yields novel gene tools for metabolic engineering. Metab Eng 2013: In press.

Huxley C, Green E D, Dunham I (1990) Rapid assessment of *S. cerevisiae* mating type by PCR. Trends Genet 6: 236.

Johnston C G, Aust S D (1994) Detection of Phanerochaete chrysosporium in soil by PCR and restriction enzyme analysis. Appl Environ Microbiol 60: 2350-2354.

Kotaka A, Sahara H, Kondo A, Ueda M, Hata Y (2009) Efficient generation of recessive traits in diploid sake yeast by targeted gene disruption and loss of heterozygosity. Appl Microbiol Biotechnol 82: 387-395.

Larsson K, Ansell R, Eriksson P, Adler L (1993) A gene encoding sn-glycerol 3-phosphate dehydrogenase (NAD+) complements an osmosensitive mutant of *Saccharomyces cerevisiae*. Mol Microbiol 10: 1101-1111.

Luyten K, Albertyn J, Skibbe W F, Prior B A, Ramos J, Thevelein J M, Hohmann S (1995) Fps1, a yeast member of the MIP family of channel proteins, is a facilitator for glycerol uptake and efflux and is inactive under osmotic stress. Embo J 14: 1360-1371.

Nevoigt E (2008) Progress in metabolic engineering of *Saccharomyces cerevisiae*. Microbiol Mol Biol Rev 72: 379-412.

Nevoigt E, Stahl U (1996) Reduced pyruvate decarboxylase and increased glycerol-3-phosphate dehydrogenase [NAD+] levels enhance glycerol production in *Saccharomyces cerevisiae*. Yeast 12: 1331-1337.

Nevoigt E, Stahl U (1997) Osmoregulation and glycerol metabolism in the yeast *Saccharomyces cerevisiae*. FEMS Microbiol Rev 21: 231-241.

Nissen T L, Hamann C W, Kielland-Brandt M C, Nielsen J, Villadsen J (2000a) Anaerobic and aerobic batch cultivations of *Saccharomyces cerevisiae* mutants impaired in glycerol synthesis. Yeast 16: 463-474.

Nissen T L, Kielland-Brandt M C, Nielsen J, Villadsen J (2000b) Optimization of ethanol production in *Saccharomyces cerevisiae* by metabolic engineering of the ammonium assimilation. Metab Eng 2: 69-77.

Olesen K, Franke Johannesen P, Hoffmann L, Bech Sorensen S, Gjermansen C, Hansen J (2000) The pYC plasmids, a series of cassette-based yeast plasmid vectors providing means of counter-selection. Yeast 16: 1035-1043.

Pagliardini J, Hubmann G, Bideaux C, Alfenore S, Nevoigt E, Guillouet S E (2010) Quantitative evaluation of yeast's requirement for glycerol formation in very high ethanol performance fed-batch process. Microb Cell Fact 9: 36.

Parts L, Cubillos F A, Warringer J, Jain K, Salinas F, Bumpstead S J, Molin M, Zia A, Simpson J T, Quail M A, Moses A, Louis E J, Durbin R, Liti G (2011) Revealing the genetic structure of a trait by sequencing a population under selection. Genome Res 21: 1131-1138.

Pasteur M L (1858) Production constante de glycérine dans la fermentation alcoolique. C R Acad Sci 46: 857.

Remize F, Roustan J L, Sablayrolles J M, Barre P, Dequin S (1999) Glycerol overproduction by engineered *Saccharomyces cerevisiae* wine yeast strains leads to substantial changes in by-product formation and to a stimulation of fermentation rate in stationary phase. Appl Environ Microbiol 65: 143-149.

Rep M, Reiser V, Gartner U, Thevelein J M, Hohmann S, Ammerer G, Ruis H: Osmotic stress-induced gene expression in *Saccharomyces cerevisiae* requires Msnlp and the novel nuclear factor Hot1p. Mol Cell Biol 1999, 19:5474-5485.

Sambrook J, Maniatis T, Fritsch E F (1989) Molecular cloning: a laboratory manual, 2nd edn. Cold Spring Harbor, N.Y.: Cold Spring Harbor Laboratory.

Sanger F, Coulson A R (1975) A rapid method for determining sequences in DNA by primed synthesis with DNA polymerase. J Mol Biol 94: 441-448.

Schuller D, Casal M (2005) The use of genetically modified *Saccharomyces cerevisiae* strains in the wine industry. Appl Microbiol Biotechnol 68: 292-304.

Shepherd A, Piper P W (2010) The Fps 1 p aquaglyceroporin facilitates the use of small aliphatic amides as a nitrogen source by amidase-expressing yeasts. FEMS Yeast Res 10: 527-534.

Sherman F, Hicks J (1991) Micromanipulation and dissection of asci. Methods Enzymol 194: 21-37.

Steinmetz L M, Sinha H, Richards D R, Spiegelman J I, Oefner P J, McCusker J H, Davis R W (2002) Dissecting the architecture of a quantitative trait locus in yeast. Nature 416: 326-330.

Swinnen S, Schaerlaekens K, Pais T, Claesen J, Hubmann G, Yang Y, Demeke M, Foulquie-Moreno M R, Goovaerts A, Souvereyns K, Clement L, Dumortier F, Thevelein J M (2012a) Identification of novel causative genes determining the complex trait of high ethanol tolerance in yeast using pooled-segregant wholegenome sequence analysis. Genome Research 22: 975-984.

Swinnen S, Thevelein J M, Nevoigt E (2012b) Genetic mapping of quantitative phenotypic traits in *Saccharomyces cerevisiae*. FEMS Yeast Res 12: 215-227.

Winzeler E A, Richards D R, Conway A R, Goldstein A L, Kalman S, McCullough M J, McCusker J H, Stevens D A, Wodicka L, Lockhart D J, Davis R W (1998) Direct allelic variation scanning of the yeast genome. Science 281: 1194-1197.

The invention claimed is:

1. A method of producing bioethanol, the method comprising:

utilizing a *Saccharomyces* spp. yeast strain for high yield bioethanol production by culturing the *Saccharomyces* spp. yeast strain in a medium, wherein the *Saccharomyces* spp. yeast strain comprises a gene encoding a truncated ssk1 protein, wherein the truncated ssk1 protein lacks the response regulator receiver domain, wherein the truncated ssk1 protein comprises at least amino acids 1-300 of SEQ ID NO: 2, and wherein the yeast strain lacks a gene encoding a wild-type ssk1 protein.

2. The method of according to claim 1, wherein the truncated ssk1 protein further comprises at least amino acids 330-356 of SEQ ID NO: 4.

3. The method according to claim 1, wherein the truncated ssk1 protein is encoded by a nucleic acid molecule comprising SEQ ID NO:3.

4. The method according to claim 1, wherein the yeast strain strain is a diploid, polyploid, or aneuploid strain, and wherein all wild-type copies of SSK1 gene have been replaced by a gene encoding the truncated ssk1 protein.

5. The method according to claim 1, wherein the yeast strain further comprises a specific allele encoding a protein selected from the group consisting of gpd1$^{L164P}$, hot1$^{P107S,H274Y}$ and smp1$^{R110Q,P269Q}$.

6. The method according to claim 1, wherein the bioethanol is produced in high osmotic media or on cellulosic hydrolysates.

7. The method according to claim 1, having a glycerol over ethanol ratio lower than 4%.

8. A method of producing ethanol of the type involving culturing a *Saccharomyces* spp. yeast strain that co-produces glycerol with the ethanol, wherein the improvement comprises:

culturing a recombinant *Saccharomyces* spp. yeast strain comprising a gene encoding a truncated ssk1 protein lacking the response regulator receiver domain and comprising at least amino acids 1-300 of SEQ ID NO: 2, wherein the *Saccharomyces* spp. yeast strain lacks a gene encoding a wild-type ssk1 protein, so as to decrease glycerol production when compared to wild-type *Saccharomyces* spp. yeast strain.

9. The method according to claim 8, wherein the ethanol is produced on cellulosic hydrolysates.

10. The method according to claim 8, wherein glycerol production is less than 0.06 g $g^{-1}$, when tested on minimal medium with 5% glucose.

* * * * *